US005566092A

United States Patent [19]
Wang et al.

[11] Patent Number: 5,566,092
[45] Date of Patent: Oct. 15, 1996

[54] MACHINE FAULT DIAGNOSTICS SYSTEM AND METHOD

[75] Inventors: Hsu-Pin Wang, Tallahassee, Fla.; Hsin-Hao Huang, Kaohsiung, Taiwan; Gerald M. Knapp, Baton Rouge, La.; Chang-Ching Lin, Tallahassee, Fla.; Shui-Shun Lin, Tallahassee, Fla.; Julie K. Spoerre, Tallahassee, Fla.

[73] Assignee: Caterpillar Inc., Peoria, Ill.

[21] Appl. No.: 176,482

[22] Filed: Dec. 30, 1993

[51] Int. Cl.$^6$ .................................................. G01B 7/00
[52] U.S. Cl. ............... 364/551.02; 364/131; 364/474.01; 364/474.11; 364/474.16; 395/904; 395/912
[58] Field of Search ................... 364/131, 164, 364/474.01, 474.11, 474.15–474.17, 505, 506, 550, 551.01, 551.02, 579, 578; 395/3, 11, 21, 22, 50, 66, 75, 77, 82–84, 88, 93, 97, 900, 903, 904, 906, 907, 909, 911, 912, 914, 915, 932, 2.25–2.28, 2.11

[56] References Cited

U.S. PATENT DOCUMENTS

| | | | |
|---|---|---|---|
| 4,803,736 | 2/1989 | Grossberg et al. | |
| 4,839,823 | 6/1989 | Matsumoto | 395/907 |
| 4,901,218 | 2/1990 | Cornwell | 364/131 |
| 4,914,708 | 4/1990 | Carpenter et al. | |
| 5,040,214 | 8/1991 | Grossberg et al. | |
| 5,121,467 | 6/1992 | Skeirik | 395/22 |
| 5,130,936 | 7/1992 | Sheppard et al. | 395/22 |
| 5,133,021 | 7/1992 | Carpenter et al. | |
| 5,142,590 | 8/1992 | Carpenter et al. | |
| 5,157,738 | 10/1992 | Carpenter et al. | |
| 5,214,715 | 5/1993 | Carpenter et al. | |
| 5,249,257 | 9/1993 | Akahori et al. | 395/3 |
| 5,303,331 | 4/1994 | Namba | 395/906 |
| 5,329,465 | 7/1994 | Arcella et al. | 395/915 |
| 5,357,449 | 10/1994 | Oh | 364/551.01 |
| 5,402,519 | 3/1995 | Inoue et al. | 395/22 |
| 5,402,520 | 3/1995 | Schnitta | 395/21 |
| 5,414,645 | 5/1995 | Hirano | 364/551.01 |

FOREIGN PATENT DOCUMENTS

0244483B1  7/1992  European Pat. Off. .
WO9213306  8/1992  WIPO .

OTHER PUBLICATIONS

Huang et al., Tandem Artmap Neural Networks for Feedback Process Control: A Welding Example, Nov. 8–13, 1992, PED–vol. 57, Neural Networks in Manufacturing and Robotics, ASME, pp. 11–22.

Ibrahim et al., A Modified Flow Enforcement Technique for Preventive Congestion Control in ATM Networks, 1993, pp. 45–53.

Carpenter et al., "Art 2: Self–Organization of Stable Category Recognition Codes for Analog Input Patterns," *Applied Optics*, vol. 26, No. 23, pp. 4919–4930, Dec. 1, 1987.

Carpenter et al., "ARTMAP: Supervised Real–Time Learning and Classification of Nonstationary Data by a Self–Organizing Neural Network," *Neural Networks*, vol. 4, pp. 565–588, 1991.

(List continued on next page.)

*Primary Examiner*—Emanuel T. Voeltz
*Assistant Examiner*—Hal P. Wachsman
*Attorney, Agent, or Firm*—Robert Sokohl

[57] ABSTRACT

The invention provides a machine fault diagnostic system to help ensure effective equipment maintenance. The major technique used for fault diagnostics is a fault diagnostic network (FDN) which is based on a modified ARTMAP neural network architecture. A hypothesis and test procedure based on fuzzy logic and physical bearing models is disclosed to operate with the FDN for detecting faults that cannot be recognized by the FDN and for analyzing complex machine conditions. The procedure described herein is able to provide accurate fault diagnosis for both one and multiple-fault conditions. Furthermore, a transputer-based parallel processing technique is used in which the FDN is implemented on a network of four T800-25 transputers.

25 Claims, 19 Drawing Sheets

OTHER PUBLICATIONS

Huang et al., "Machine Fault Classification Using an ART 2 Neural Network," Nov. 1991, Accepted for International Journal of Advance Manufacturing Technology, May 1992.

Huang et al., "Artmap Neural Networks for Closed–Loop Welding Process Control," to appear in *Artificial Intelligence in Optimal Design and Manufacturing*, edited by Z. Dong, Oct. 1992.

Spoerre, Julie K., "Machine Performance Monitoring and Fault Classification Using an Exponentially Weighted Moving Average Scheme," Thesis, May 1993.

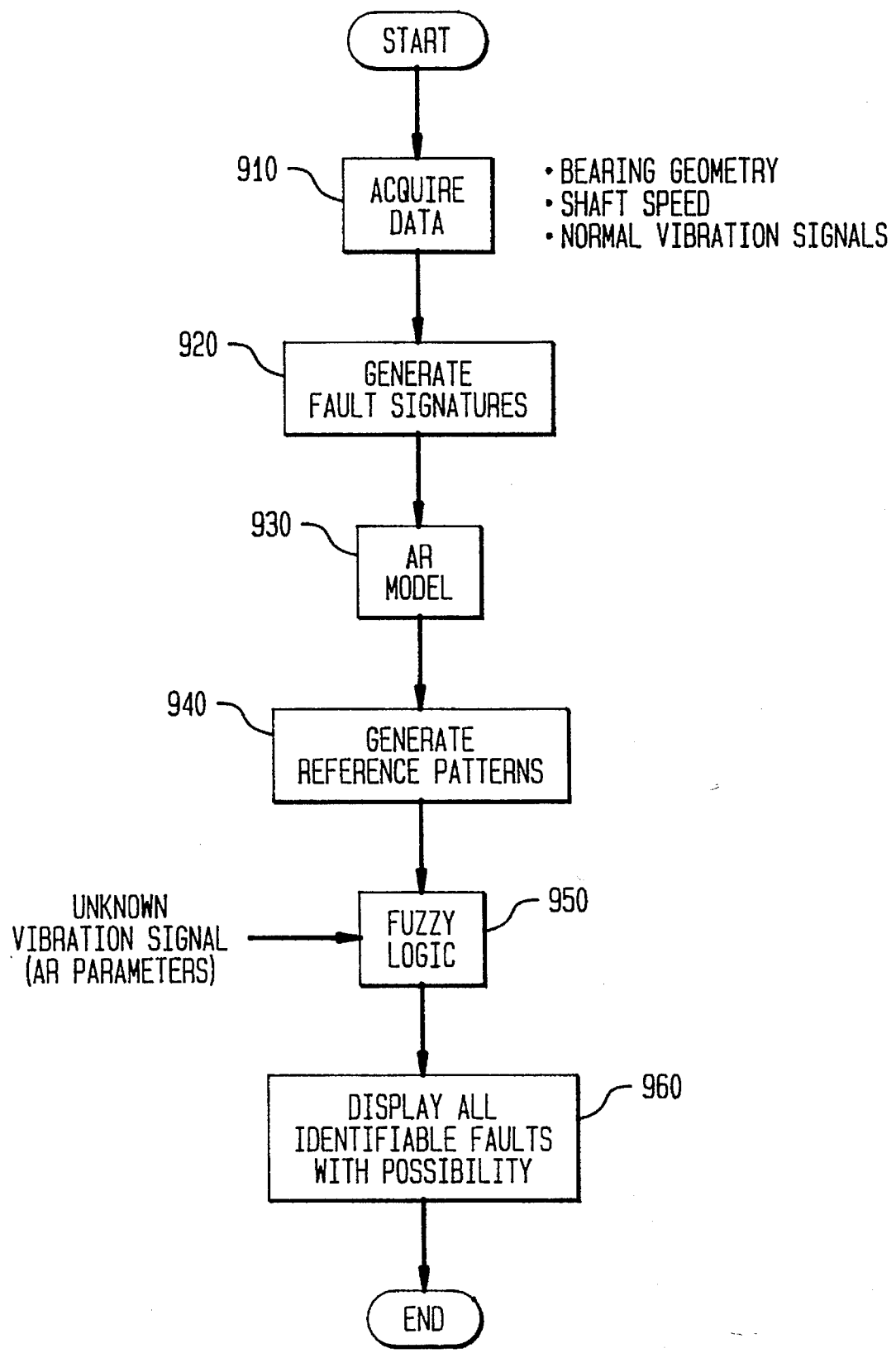

ONE TRANSPUTER

TWO TRANSPUTERS

THREE TRANSPUTERS

ONE TRANSPUTER

INNER RACE + OUTER RACE
ROLLER SPIN + CAGE DEFECT
IMBALANCE + MISALIGNMENT

THREE TRANSPUTERS

INNER RACE + OUTER RACE

ROLLER SPIN + CAGE DEFECT

IMBALANCE + MISALIGNMENT

ONE TRANSPUTER

FIRST POSSIBLE FAULT
+
SECOND POSSIBLE FAULT

TWO TRANSPUTERS

FIRST POSSIBLE FAULT

SECOND POSSIBLE FAULT

MACHINE FAULT DIAGNOSTICS SYSTEM AND METHOD

Cross-Reference to Co-Pending Applications

The following applications are assigned to the assignee of the present application:

U.S. Patent Application entitled "Supervised Training of a Neural Network," Ser. No. 08/176,458, naming as inventors Hsin-Hoa Huang, Shui-Shun Lin, Gerald M. Knapp, and Hsu-Pin Wang, filed concurrently herewith, pending the disclosure of which is hereby incorporated by reference in its entirety.

U.S. Patent Application entitled "Machine Performance Monitoring and Fault Classification Using an Exponential Weighted Moving Average Scheme," Ser. No. 08/176,456, naming as inventors Julie M. Spoerre, Chang-Ching Lin, and Hsu-Pin Wang, filed concurrently herewith, pending the disclosure of which is hereby incorporated by reference in its entirety.

BACKGROUND OF THE INVENTION

1. Field of the Invention

The present invention relates generally to the field of machine fault diagnostics and, more particularly, to a system and method that uses predictive maintenance for on-line, real time monitoring of mechanical components for possible failures.

2. Related Art

Over the past few decades industry has taken a variety of steps to improve productivity and quality. However, little attention has been given to the area of maintenance. Maintenance in a broad definition is concerned with controlling the condition of equipment. Although maintenance exists in virtually every manufacturing company, it is often considered to be a support function of a manufacturing process. Only in recent years has maintenance been recognized as an integral part of the manufacturing process, able to increase productivity and quality.

With the increased use of robots, automation, and more sophisticated machines in manufacturing processes, it might be more appropriate to say that productivity and quality depend on machines rather than the person who operates the machine. Robots, for example, have replaced human operators in tasks, such as assembly, loading and unloading, spot welding, and inspection. Keeping this sophisticated equipment in a satisfactory condition increases both the amount and complexity of maintenance. Hence, more repair time and more highly trained, high-priced maintenance technicians and engineers are needed. This, of course, translates to higher maintenance costs.

When the degree of automation increases, maintenance cost also increases. In many companies, maintenance costs represent one of the larger parts of total operating costs - often more than direct labor cost. Therefore, a maintenance strategy that effectively reduces maintenance cost is important for a modern industry to remain competitive.

The three most common maintenance strategies are breakdown or corrective maintenance (i.e., fix the machine when it fails), preventive or time-based maintenance (i.e., maintain machine based on scheduled time), and predictive or condition-based maintenance (i.e., maintain machine before it fails).

For many years, most manufacturing companies used either breakdown or preventive maintenance. In such a case, the machinery is either allowed to breakdown or routine maintenance is performed to reduce the risk of machine failures. Nevertheless, breakdown maintenance is suitable only when a machine is not important, and is inexpensive to replace. If the cost of lost production, potential secondary damage to machinery, and potential safety risks are high, then this strategy is unacceptable. An apparent improvement to this strategy is to use preventive maintenance.

Although preventive maintenance can reduce the occurrence of machine breakdown, it also has some problems. First, the period between overhauls is very difficult to determine because machines and their components do not necessarily fail at regular intervals. Second, precious production time is lost because it is prudent to examine as many components as possible during the overhaul period. Third, parts in reasonable condition are often replaced unnecessarily.

Therefore, the best strategy appears to be to adopt a predictive maintenance strategy which predicts the condition, performance, and reliability of machinery, so that maintenance can be planned in advance. Recently, due to the increasing requirement of product quality and manufacturing automation, more and more manufacturing companies have adopted predictive maintenance as part of their maintenance program. They are doing so in order to increase reliability, productivity, and availability while minimizing costs of maintenance and overall plant operation.

Machine monitoring and diagnostics can be seen as a decision-support tool which is capable of identifying the cause of failure in a machine component or system, as well as predicting its occurrence from a symptom. Without accurate direction and identification of the machine fault, maintenance and production scheduling cannot be effectively planned and the necessary repair task cannot be carried out in time. Therefore, machine monitoring and diagnostics is essential for an effective predictive maintenance program.

The ultimate goal of using machine monitoring and diagnostics is to increase equipment availability, and in addition, reduce maintenance and unexpected machine breakdown costs. In order to maximize availability, one has to increase reliability by maximizing the mean time between failures and, at the same time, increase maintainability by minimizing the mean time to repair. As a result of constant monitoring and diagnostics, the frequency of unexpected machine breakdown is significantly reduced, and machine failure can be pinpointed immediately. As a result, reliability and maintainability are increased.

Machine monitoring and diagnostics can be done by simply listening to the sound generated during machine operation or visually examining the quality of machined parts to determine machine condition. In such a situation, however, the identification of a machine fault is totally dependent on the experience of the operator or engineer. Besides, many machine faults are not accurately assessed by relying only on visual or aural observations, especially during operation (e.g., wear and crack in bearings and gearboxes). Therefore, more sophisticated signal processing techniques, such as vibration analysis, oil analysis, acoustic emission, infrared, and ultrasound, have been developed to help the maintenance technician and engineer detect and diagnose machine failures.

The type of signal processing technique to be used for machine monitoring and diagnostics depends on the type of machine parameter to be monitored, as well as the type of fault to be tackled. There are a number of machine parameters which can be monitored, such as vibration, sound, temperature, force, pressure, motor current, lubricant oil, etc. Many studies have been conducted to determine which are most effective. Unfortunately, no parameter is able to indicate the full range of machine faults.

It is well-known that using a number of machine parameters in combination can produce a more accurate and reliable indication of machine condition. In such a case, maintenance personnel must be familiar with a number of different signal processing techniques, as well as their ability to detect certain types of faults. In addition, a large amount of data must be collected, analyzed, and understood. This means more time and knowledge are required for maintenance personnel to make a correct diagnosis.

Over the last two decades, most of the machine monitoring and diagnostic systems have been performed off-line using signal processing techniques. The success of these systems is not due to any one signal processing technique, but to the large amount of redundancy associated with multiple signal processing.

However, those signal processing techniques are very complicated to use; in addition, they must be performed by a highly trained and experienced human analyzer in order to make an accurate diagnosis. Accurate fault diagnostics is essential, especially in reducing product cycle time. As a result of correct and rapid fault diagnostics, equipment maintainability and availability can be improved significantly, thereby reducing the product cycle time. Although many new technologies, such as expert system, fuzzy sets, pattern recognition, and artificial neural networks, have been proposed to help achieve this goal, there is still no universal method available since each method has various capabilities and limitations.

Given below is a discussion of the four most prevalent techniques for machine monitoring and diagnostics—signal processing (e.g., vibration analysis and parametric modeling), artificial intelligence, artificial neural network, and sensor fusion.

Over the years, most machine monitoring and diagnostic systems have been performed by gathering the sensory data from the process, then analyzing the data off-line through a signal processing technique. One of the most widely used signal processing techniques is vibration analysis. This is because no other parameter can reveal as wide a range of machine fault types as vibration.

Vibration analysis deals with the extraction of information from measured vibration signals. It is well recognized that vibration characteristics will change as a machine condition changes. Wear or damage to rotating elements, imbalance, and resonance can generate excessive vibration.

Generally, vibration data can be analyzed in two different domains: time and frequency (J. Tranter, "The Fundamentals of, and The Application of Computer to, Condition Monitoring and Predictive Maintenance,", *Proceedings of the 1st International Machinery Monitoring and Diagnostics Conference and Exhibit*, Las Vegas, Nev., September 1989, pp. 394–401, and C. J. Li and S. M. Wu, "On-Line Detection of Localized Defects in Bearings by Pattern Recognition Analysis," *Journal of Engineering of Industry*, Vol. 111, November 1989, pp. 331–336). Time-domain analysis involves designing indices that are sensitive to the amount of impulsive vibrations observed. This technique includes overall level (RMS) measurements, peak level detection, crest factor, shock pulse, spike energy, kurtosis analysis, time waveform, and orbits. Frequency-domain analysis involves transforming the vibration waveform to show a train of impulses at different frequencies. This technique includes spectrum analysis, waterfall plot, cepstrum analysis, difference spectra, RMS of spectral difference, envelope analysis, high frequency resonance analysis (HFRT), and matched filter.

One of the most powerful vibration analysis techniques is spectrum analysis, which estimates the spectrum or power spectral density (PSD) from a vibration signal by performing a Fast Fourier Transform (FFT). The reason for the popularity of this FFT-based technique is because of its high computational speed. In addition, analysis of a machine vibration spectrum can yield important information regarding the condition of machine components because each rotating component in a machine generates identifiable frequencies; thus, changes at a given frequency range can be related directly to a specific component failure. However, there are some problems with this FFT-based technique, including low frequency resolution, implicit windowing of the data, and no significant data reduction.

In addition to spectrum analysis, the parametric modeling technique has been used for estimating the vibration spectrum. It is used in an attempt to alleviate the inherent limitations of the FFT approach mentioned above. Two major advantages of using a parametric modeling technique are: improvement of frequency resolution over FFT by suppressing the noise from the real signal, and reduction of data by using few parameters to describe the signal globally.

A number of parametric modeling techniques have been reported to estimate the vibration spectrum, for example, the autoregressive (AR) method, the autoregressive and moving average (ARMA) method, Prony's method, the minimum variance method, and the covariance method. A detailed review of these techniques can be found in (S. M. Kay and S. L. Marple, "Spectrum Analysis—A Modern Perspective," *Proceedings of the IEEE*, Vol. 69, No. 11, November 1981, pp. 1380–1419, and S. Braun, *Mechanical Signature Analysis: Theory and Applications*, Academic Press, London, 1986).

The parametric methods described above have been applied in the area of fault detection (see, e.g., Matsushima et al., "In-Process Detection of Took Breakage by Monitoring the Spindle Current of a Machine Tool," *Proceedings of ASME Winter Annual Meeting*, Phoenix, Ariz., 1982, pp. 145–154; M. Sidahmed, "Contribution of Parametric Signal Processing Techniques to Machinery Condition Monitoring," *Proceedings of the 1st International Machinery Monitoring and Diagnostics Conference and Exhibit*, Las Vegas, Nev., September 1989, pp. 190–195, S. Y. Liang and D. A. Dornfeld; "Tool Wear Detection Using Time Series Analysis of Acoustic Emission," *Journal of Engineering for Industry*, Vol. 111, August 1989, pp 199–205; Wu et al., "Signature Analysis for Mechanical Systems via Dynamic Data System (DDS) Monitoring Technique," *Journal of Mechanical Design*, Vol. 102, April 1980, pp. 217–221).

The disadvantage of parametric modeling is that it is not easy to find an optimal order for the model. The general guideline in the selection of the model order is based on the minimization of the sum of square errors. H. Akaike, "Power Spectrum Estimation through Autoregression Model Fitting,": *Ann. Inst. Stat. Math.*, Vol. 21, 1969, pp. 407–419 and "A New Look at the Statistical Model Identification," *IEEE Trans. Autom. Control*, Vol. AC-19, December 1974, pp. 716–723, proposed two criteria, final prediction error (FPE) and Akaike information criterion (AIC), which can be used as the objective functions for order selection. In the recent work of C.C. Lin, "Classification of Autoregressive Spectral Estimated Signal Patterns Using an Adaptive Resonance Theory (ART)," Master's Thesis, Department of Industrial Engineering, The University of Iowa, Iowa City, August 1992, the order with the highest FPE and AIC level was selected as the optimal order.

Both parametric models mentioned above performed well in the early detection of machine failure. However, they are unable to identify the cause of the failure. This fault recognition task is usually done by the analyzer who identifies the cause of the fault by visual inspection of the spectrum. This is not an easy task because it requires experience and knowledge in order to make a correct diagnosis.

Although vibration analysis and parametric modeling techniques have been proven to be useful for machine monitoring and diagnostics, they are also knowledge-intensive techniques. In other words, they need to be performed by a highly trained and experienced engineer in order to identify the source of the machine fault correctly. To overcome this problem, an artificial intelligence approach has been proposed. In the past few years, the application of artificial intelligence to fault diagnostics has received much attention. Two of the most popular artificial intelligence approaches are expert systems and model-based reasoning.

One of the biggest successes in the field of artificial intelligence is expert systems. An expert system is a computer system which is programmed to exhibit expert knowledge in solving a particular domain problem. A typical expert system consists of the following components:

knowledge base (which contains knowledge about the problem, i.e., rules and facts), inference engine (which is the method for combining rules and facts to reach conclusions), explanation component (which explains why and how the conclusions are reached), user interface (which includes knowledge and data acquisition).

Generally, the knowledge is represented in the form of an "if-then" rule. This rule is based on problem-solving heuristics generated by the expert. The inference engine controls the use of the knowledge base. Its control strategy can initiate from the facts or symptoms to reach a conclusion (forward chaining), or from a possible conclusion and search through the facts to verify the conclusion (backward chaining).

Many expert systems have been developed during the past several years for machine diagnostics. A detailed survey of fault diagnostic expert systems can be found in (S. G. Tzafestas, "System Fault Diagnosis Using the Knowledge-Based Methodology," *Fault Diagnostics in Dynamic Systems: Theory and Applications*, edited by R. Patton, P. Frank, and R. Clark, Prentice-Hall, New York, 1989).

Although expert systems are easy to use and able to provide expert knowledge to solve a specific domain problem, there are many difficulties in using this approach (J. M. David and J. P. Krivine, "Three Artificial Intelligence Issues in Fault Diagnosis: Declarative Programming, Expert Systems, and Model-Based Reasoning," *Proceedings of the Second European Workshop on Fault Diagnostics, Reliability and Related Knowledge Based Approaches*, UMIST, Manchester, Apr. 6–8, 1987, pp. 19–196), such as: difficulty in formalizing the problem, difficulty in obtaining knowledge, and difficulty in validating the system. In addition, there are many drawbacks with building an expert system for machine monitoring and diagnostics. One of the major drawbacks is its long execution time. This is particularly true when complex relations and a large knowledge base are involved in the reasoning process. Because expert systems must work through complex chains of reasoning in order to reach a conclusion, more processing time is required. Hence, the short response time required to perform on-line machine monitoring and diagnostics makes the application of expert systems in this area difficult and impractical.

As an alternate approach to expert systems, model-based reasoning has been proposed to solve diagnostic reasoning problems. One of the most promising techniques of model-based reasoning is "reasoning from structure and behavior" (R. Davis, "Diagnostic Reasoning Based on Structure and Behavior," *Artificial Intelligence*, Vol. 24, 1984, pp. 347–410). This technique begins with a description of the system, together with the observation(s) of the system behavior. If the observation conflicts with the way the system is meant to behave, then one concludes that a system failure has occurred. Given symptoms of misbehavior, possible fault candidates are identified using the structural model by following a dependency chain back from a violated prediction to each component that contributed to that prediction.

Many of the notable applications of model-based reasoning to diagnostic problems have been in the digital electronics field. This is because the structure of digital circuits can be represented in a fairly obvious way, and the intended behavior of the circuit is strongly implied by its structure.

Compared to the expert system approach, knowledge acquisition for the model-based system is easier. In addition, the model-based system is more robust and maintainable. It is able to diagnose multiple faults, avoiding exponential growth in the model size. However, it still poses problems for real-time diagnosis because the system has to look for all possible fault candidates and then has to classify them one by one according to likelihood, which means more reasoning time is needed.

The identification of a machine or component fault is actually a pattern recognition problem. In the past, a number of pattern recognition techniques, such as linear discriminant function and fuzzy sets, have been applied to solve this type of problem. Normally, these techniques classify machine or component condition into a two-state situation, i.e., normal or abnormal. Recently, artificial neural networks have been applied successfully in the area of machine monitoring and diagnostics. See for example, Dietz et al., "Jet and Rocket Engine Fault Diagnosis in Real Time," *Journal of Neural Network Computing*, 1989, pp. 5–18, Marko et al., "Automotive Control System Diagnostics Using Neural Nets for Rapid Pattern Classification of Large Data Sets,":, *Processing of International Joint Conference on Neural Networks* (ICJNN), Vol. II, 1989, pp. 13–15, Sunil et al., "Machining Condition Monitoring for Automation Using Neural Networks," *Monitoring and Control for Manufacturing Processes*: Presented at the Winter Annual Meeting of the ASME, Dallas, Tex., Nov. 25–30, 1990, pp. 85–100, Hoskins et al., "Incipient Fault Detection and Diagnosis Using Neural Networks," Proceedings of the International Joint Conference on Neural Networks (IJCNN), Vol. 1, 1990, pp. 81–86, T. I. Liu and E. J. Ko, "On-Line Recognition of Drill Wear via Artificial Neural Networks," *Monitoring and Control for Manufacturing Processes*: Presented at the Winter Annual Meeting of the ASME, Dallas, Tex., Nov. 25–30, 1990, pp. 101–110, Y. Guo and K. J. Dooley, "The Application of Neural Networks to a Diagnostic Problem in Quality Control," *Monitoring and Control for Manufacturing Processes*: Presented at the Winter Annual Meeting of the ASME, Dallas, Tex., Nov. 25–30, 1990, pp. 111–119, T. I. Liu and J. M. Mengel, "Detection of Ball Bearing Conditions by an A.I. Approach," *Proceedings of the Winter annual Meeting of the ASME*, Atlanta, Ga, Dec. 1–6, 1991, pp. 13–21, and G. M. Knapp and H. P. Wang, "Machine Fault Classification: A Neural Network Approach," *International Journal of Production Research*, Vol. 30, No. 4, 1992, pp. 811–823.

One of the greatest problems with artificial neural networks is that neural networks never explain themselves. In order to eliminate this so-called "black box" approach to neural network applications, it is necessary to build an explanation capability into a neural network system. An apparent approach is to combine expert systems and neural networks into a hybrid system. Examples of combining expert systems and neural networks can be found in M. Caudill, "Using Neural Nets: Hybrid Expert Networks," AI Expert, November 1990, pp. 49–54, D. V. Hillman, "Integrating Neural Nets and Expert Systems," AI Expert, June 1990, pp. 54–59, Kraft et al., "Hybrid Neural Net and Rule Based System for Boiler Monitoring and Diagnosis," *Proceedings of the 53rd Annual Meeting of the American Power Conference*, Chicago, Ill., Apr. 29–May 1, 1991, pp. 952–957 and Rabelo et at., "Synergy of Artificial Neural Networks and Knowledge-Based Expert Systems for Intelligent FMS Scheduling," *Proceedings of the International Joint Conference on Neural Networks* (IJCNN), Vol. 1, 1990, pp. 359–366.

Sensor fusion, sometimes referred to as multisensor integration, is a process of integrating the information obtained from a variety of sensors. It is utilized with the hope of achieving human-like performance (i.e., the ability to effectively combine information from his or her senses) in decision-making, especially in applications of image or signal processing where the information from individual sensors are generally noisy, uncertain, and insufficient.

There are four key advantages of using sensor fusion. First, fusion of redundant information obtained from a group of sensors (or a single sensor over time) concerning the same feature can increase accuracy as well as enhance reliability in the case of sensor error or failure. Second, the complementary information can be yielded by using multiple sensors to measure different aspects of the feature if the required information could not be obtained by individual sensors acting alone. Third, multiple sensors can provide more timely information, as compared to the speed at which it could be provided by a single sensor, particularly when parallelism is involved in the integration process. Fourth, multiple sensors can provide required information at a lower cost when compared to the equivalent information obtained from individual sensors. (See J. M. Fildes, "Sensor Fusion for Manufacturing," *Sensors*, January 1992, pp. 11–15, and R. C. Luo and M. G. Kay, "Multisensor Integration and Fusion: Issues and Approaches," *Sensor Fusion*: Proceedings of the SPIE, Vol. 931, 1988, pp. 42–49).

The objective of sensor fusion is to combine individual information into a representative pattern that provides a higher level of information than the sum of the information from individual sensors. The information from individual sensors can be raw data or processed data. The processed data is normally generated by a preprocessing procedure which performs pattern recognition, noise filtering, or data reduction. It can be in the form of either estimates of parameters (such as parameters of autoregressive model), or evidence supporting certain propositions, or decisions favoring certain hypotheses.

Determining a method to integrate different types of sensors in order to provide reliable and consistent information is the most challenging task in sensor fusion. However, a large number of methods are available to achieve this task. These methods extend from low-level probability distributions for statistical inference to high-level production rules for logical inference. See R. C. Luo and M. G. Kay, "Multisensor Integration and Fusion: Issues and Approaches," Sensor Fusion: Proceedings of the SPIE, Vol. 931, 1988, pp. 42–49, for a review of six general methods for sensor fusion. Additionally, G. Chryssolouris and M. Domroese, "Sensor Integration for Tool Wear Estimation in Machining," *Sensors and Controls for Manufacturing*: presented at the Winter Annual Meeting of the ASME, Chicago, Ill., Nov. 27–Dec. 2, 1988, pp. 115–123, and "An Experimental Study of Strategies for Integrating Sensor Information in Machining," Annals of the CIRP, Vol. 38, No. 1, 1989, pp. 425–428, provide a review and comparison of four different methods for sensor fusion, and conclude that a neural network approach is more effective in learning a relationship for providing parameter estimates, particularly when the relationship between the sensor-based information and the actual parameter is nonlinear; and a neural network approach is less sensitive to deterministic errors in the sensor-based information than the other three approaches.

Several popular approaches in the area of machine monitoring and diagnostics have been discussed above. Each approach has its strengths and weaknesses. A significant amount of research has been conducted in the development and application of each individual approach. However, little has been done in incorporating these different approaches into an intelligent system.

SUMMARY OF THE INVENTION

The present invention provides on-line, real-time monitoring of machine components for possible failures. A machine diagnostic system is disclosed that integrates several different technologies to detect possible failure conditions in a physical machine or process, and alert maintenance personnel. The machine diagnostic system includes the integration of neural networks, expert systems, physical models, and fuzzy logic.

The major technique used for fault diagnostics is a fault diagnostic network (FDN) which is based on a modified ARTMAP neural network architecture. The modified ARTMAP network is an efficient and robust paradigm which has the unique property of incremental learning. Unlike other popular neural networks, such as back propagation, the modified ARTMAP network does not have to be trained with all the patterns, old and new, every time a new pattern is discovered.

The modified ARTMAP network includes an ART module that accepts an input pattern. An ART 2 neural network is used as the underlying ART module. The ART module is connected to a map field that accepts as an input a target output pattern. The map field performs a mapping between a recognition category supplied by the ART module and the target output pattern. The map field also triggers a vigilance test that determines the closeness between the recognition category and the target output pattern. During the training of the modified ARTMAP network, both the input pattern and the desired output pattern are presented to the modified ARTMAP network. During the network testing phase, only the input pattern is provided.

Additionally, this invention incorporates a hypothesis and test procedure that utilizes physical models and fuzzy logic to provide further diagnostic capabilities. The hypothesis and test procedure complements the FDN. Physical models and fuzzy logic greatly enhance the diagnostic capability of the diagnostic system since the FDN does not contain the deep knowledge nor reasoning capability necessary for analyzing and pinpointing all unknown fault situations. As such, the physical models and fuzzy logic is used in two ways: 1) as a means to provide preliminary training of the diagnostic network for common faults, based on theoretical predictions, and 2) to provide a sophisticated off-line diagnostic capability for infrequently encountered and complex fault conditions.

In a preferred embodiment, the machine diagnostics system is implemented with a Fault Reasoning Expert System (FRES). Any data sample with a suspected abnormal condition not detected with full confidence by the modified ARTMAP network is sent to the FRES for analysis. Similarly, if the modified ARTMAP suspects more than one type of fault (e.g., out of alignment and contamination) then the data sample is sent to the FRES. The FRES checks the identifiable fault(s) against it rules in its knowledge base, damage or repair history, and machine usage information to determine likely faults.

The requirement of rapid processing in an on-line system motivated the inclusion of parallel processing. As such, a transputer-based parallel processing technique is disclosed. The FDN is implemented on a network of four T800-25 transputers.

BRIEF DESCRIPTION OF THE FIGURES

The above and further advantages of this invention may be better understood by referring to the following description taken in conjunction with the accompanying drawings, in which:

FIG. 9 illustrates a fuzzy logic based hypothesis and test procedure implemented according to the preferred embodiment of the present invention.

DETAILED DESCRIPTION OF THE PREFERRED EMBODIMENTS

1. Overview

The present invention provides on-line, real-time monitoring of machine components for possible failures. A machine diagnostic system is disclosed that uses neural networks, expert systems, physical models, and fuzzy logic to detect possible failure conditions and alert maintenance personnel.

Figure 4:
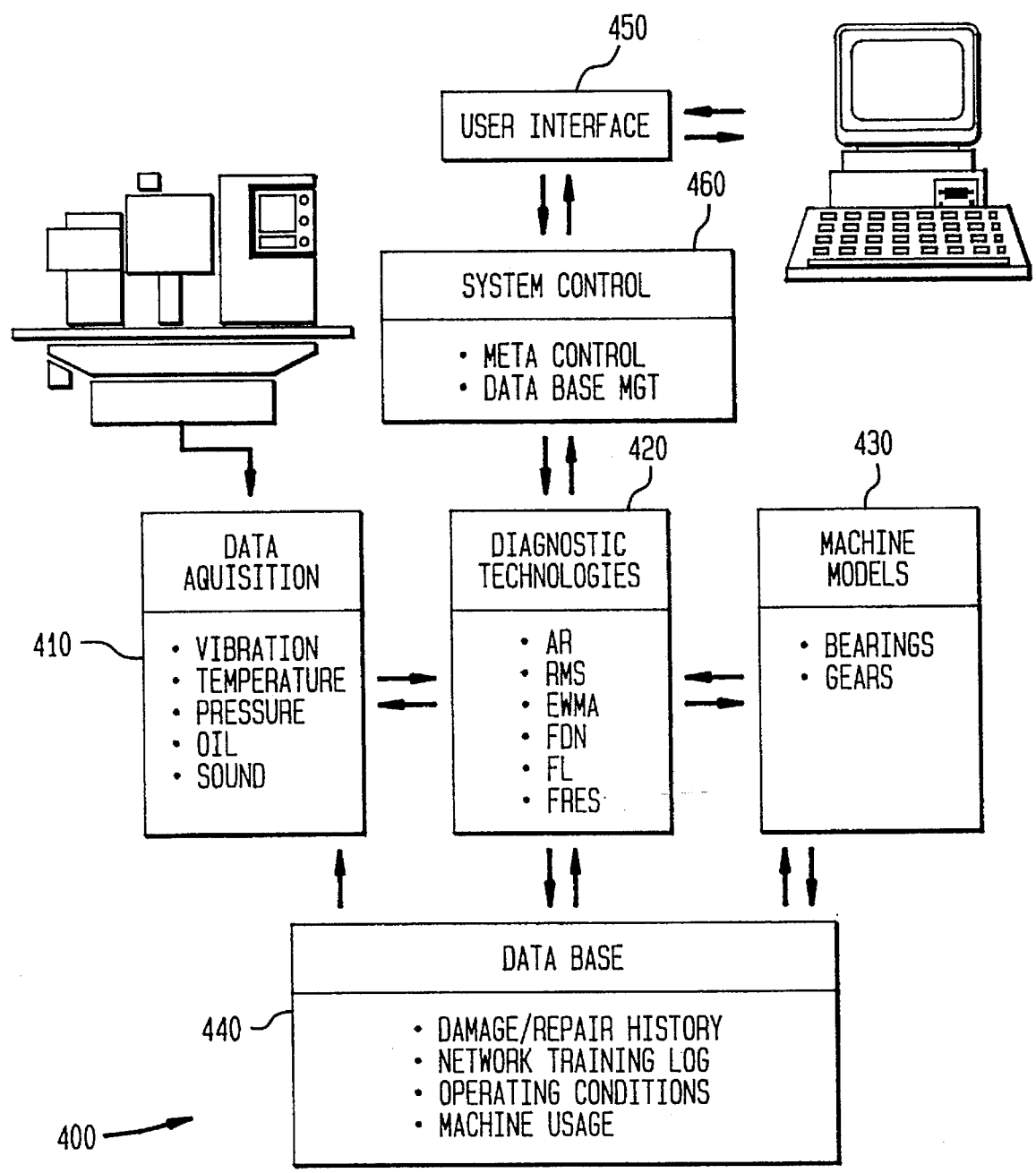
FIG. 4 shows a high level block diagram of an integrated machine monitoring diagnostic system.

FIG. 4 shows a high level block diagram of an integrated machine monitoring diagnostic system 400. The diagnostic system 400 is comprised of six modules: a dam acquisition module 410, a diagnostic technologies module 420, a machine model module 430, a database module 440, a user interface 450, and a system control module 460.

The dam acquisition module 410 collects sensory signals, such as vibration, pressure, and temperature, from the machine. It consists of a number of sensors (e.g., accelerometers, acoustic emission sensors, pressure transducer, thermal couples, etc.) and data acquisition hardware and software programs for real-time dam collection. The diagnostic technology module 420 performs on-line fault detection, fault diagnostics and provides expert recommendations by employing a number of different technologies, such as parametric modeling, a neural network, fuzzy logic, and an expert system. The machine model module 430, including physical models for bearings and gears, provides data for preliminary training of the neural network on common bearing and gear faults. In addition, the machine model module 430 provide a deep fault reasoning mechanism to identify complex or multiple fault conditions.

The database module 440 contains important system information including damage or repair history, neural network training logs, operating conditions, and machine usage. The user interface model 450 provides a friendly environment for the user to interact with the system. Its function includes displaying machine status and information, accepting user's input, etc. The system control module 460 controls and coordinates the activities among modules. It also controls the database management activity.

Figure 7:
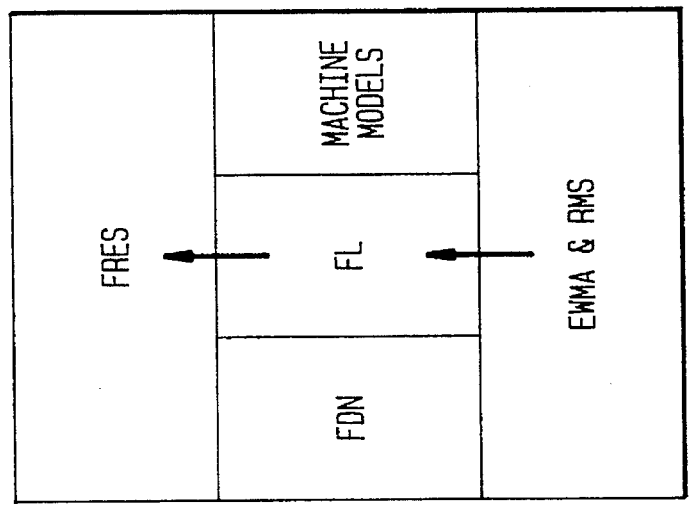
FIG. 7 illustrates three levels of fault diagnostics that are used by the present invention.

Diagnostic system 400 preprocesses sensory inputs, such as vibration and sound, using an autoregressive (AR) model. Once the data is processed, the fault diagnostics can be carried out in three different levels, as shown in FIG. 7. At the fault detection level 710, indices based on an overall root mean square (RMS) measurement and a covariance statistic of an exponentially weighted moving average (EWMA) method are used to detect an abnormal machine condition on-line. A control limit is set for each RMS or EWMA index. An abnormal condition is detected whenever the RMS or EWMA measurement of new sensory data exceeds a respective control limit. The sensory data are then transferred to the fault identification level 720 for further analysis. EWMA is described below in more detail and in Spoerre, J. K., "Machine Performance Monitoring and Fault Classification Using an Exponentially Moving Average Scheme," Masters Thesis, The University of Iowa, May 1993. RMS is well known in the art and for the sake of brevity will not be described in detail herein.

At the fault identification level 720, a fault diagnostic network (FDN) is employed to identify machine faults from the sensory data. Additional sensory data may be acquired in order to improve diagnostic accuracy. If the fault diagnostic network is not able to generate any hypothesis, a model-based reasoning approach will be applied to reason through the machine models to find possible faults. The fault reasoning of the machine models is accomplished by using the fuzzy logic (FL) methodology. The output of this reasoning process is identifiable faults and their possibilities.

Figure 15A:
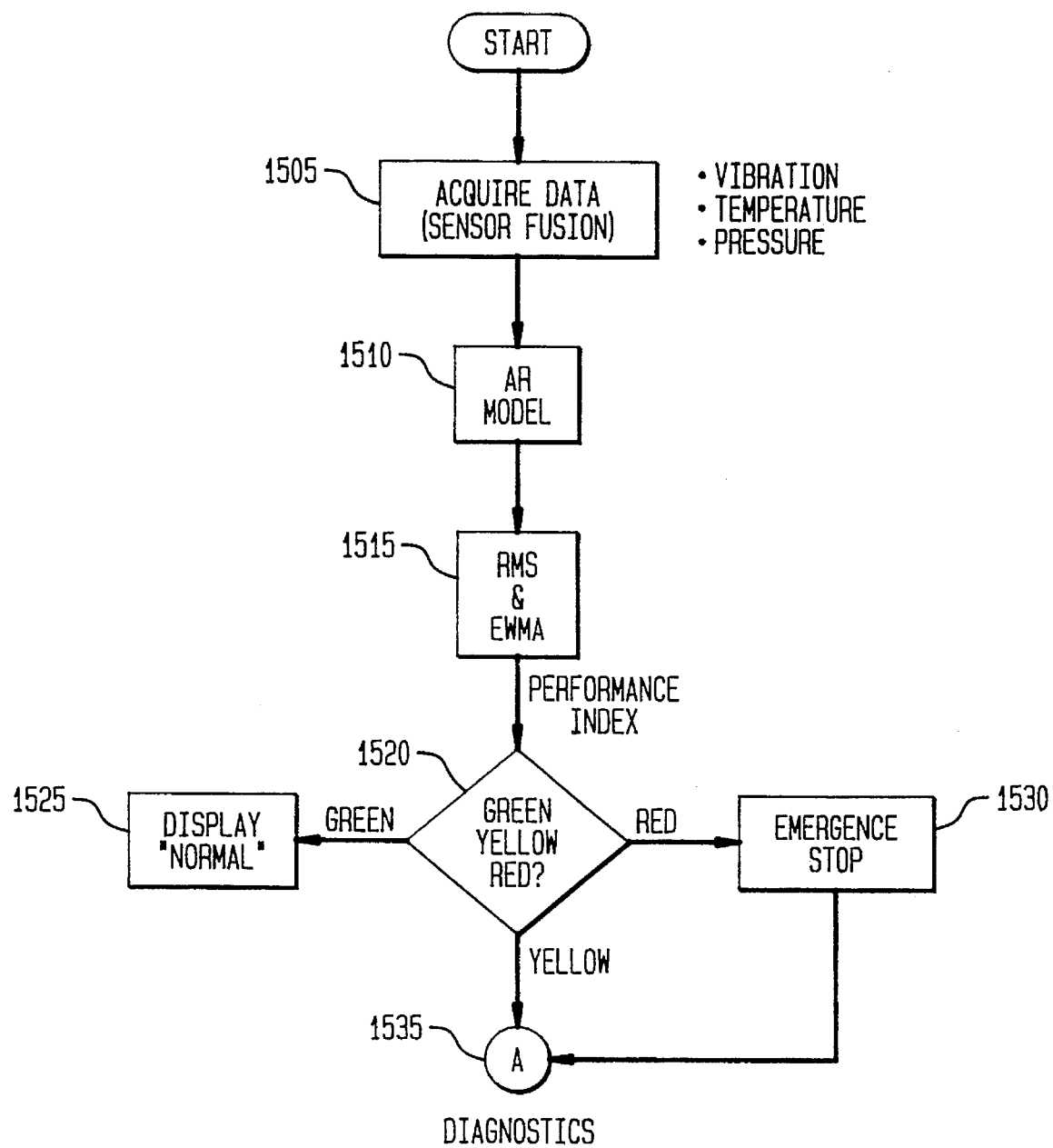
FIGS. 15A and 15B show a flowchart for a fault diagnostic procedure for an integrated system designed in accordance with the present invention.
Figure 15B:
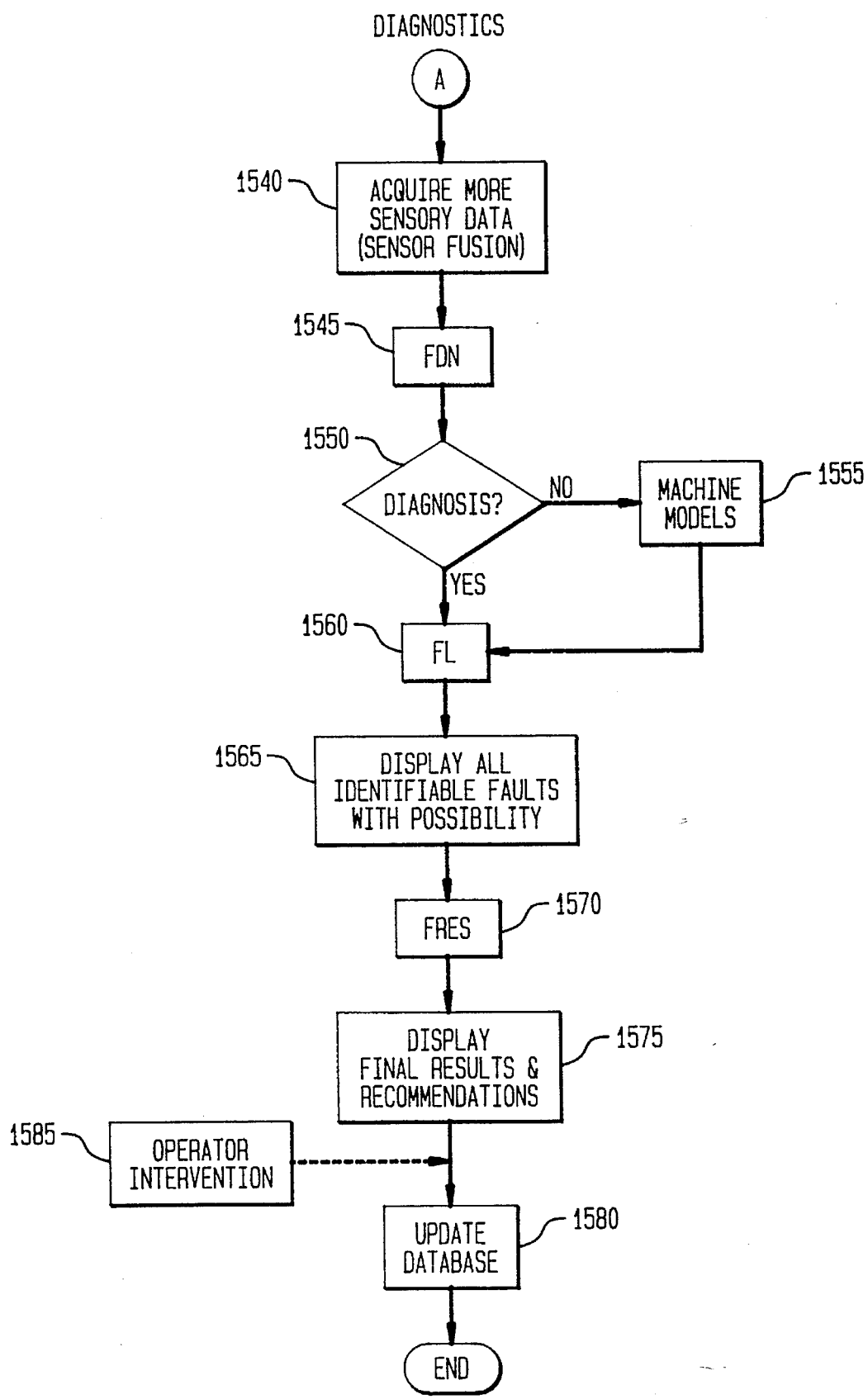

At the level of verification and recommendations 730, all the identifiable faults are verified through the fault reasoning expert system (FRES). FRES checks the faults against its rules in the knowledge base, the damage or repair history, and machine usage information to determine the most likely faults. Finally, recommendations for correcting the identified machine faults are provided by the FRES to the user. The user then can examine the machine according to the system's recommendations and store the diagnostic information in the database 440. The fault diagnostic procedure for this integrated system is shown in detail in a flowchart illustrated in FIGS. 15A and 15B; FIGS. 15A and 15B are described in detail in Section 4.5.

Figure 1:
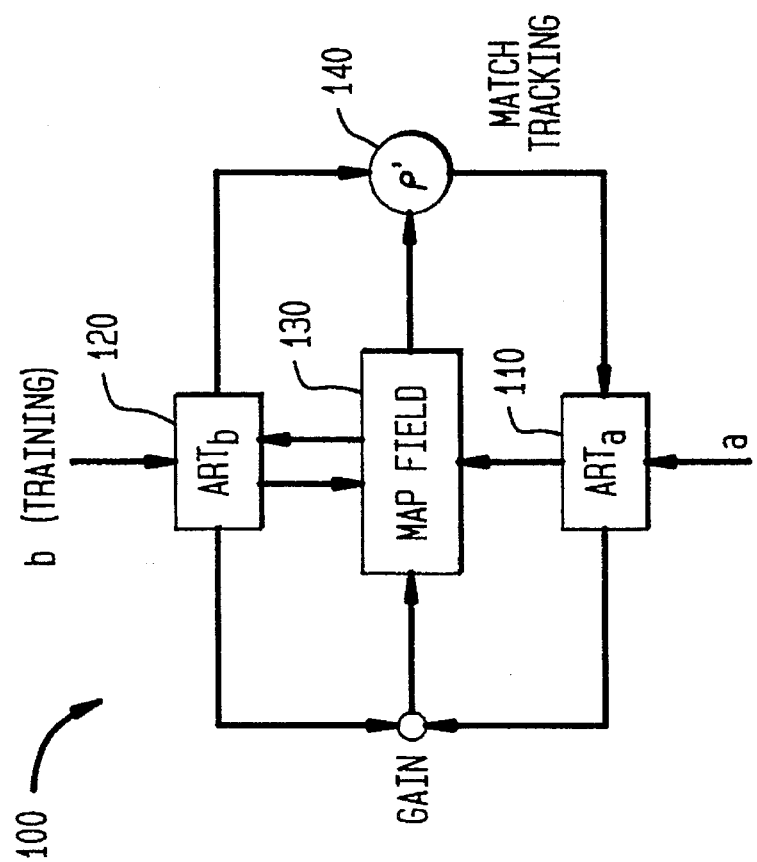
FIG. 1 illustrates a neural network architecture called Predictive Adaptive Resonance Theory (ART) or ARTMAP.

Referring to FIG. 1, the present invention employs a neural network architecture 100 called Predictive Adaptive Resonance Theory (ART) or ARTMAP, that autonomously learns to classify arbitrarily ordered vectors into recognition categories based on predictive success. See Carpenter, G. A., Grossberg, S., and Reynolds, J., "ARTMAP: Supervised Real-time Learning and Classification of Nonstationary Data by a Self-Organizing Neural Network," *Neural Networks*, Vol 4, 1991, pp. 569–588. This supervised learning system 100 is built from a pair of ART modules ($ART_a$ 110 and $ART_b$ 120) that are capable of self-organizing stable recognition categories in response to arbitrary sequences of input patterns.

Two classes of ART modules have been developed by Carpenter and Grossberg (Carpenter, B. A. and Grossberg, S. "A Massively Parallel Architecture for a Self-Organizing Neural Pattern Recognition Machine," *Computer Vision, Graphics, and Image Processing*, Vol. 37, 1987, pp. 54–115 and Carpenter G. A. and Grossberg, S., "ART 2: Self Organization of Stable Category Recognition Codes for Analog Input Patterns," *Applied Optics*, Vol 26, No. 23, 1987, pp. 4919–4930; ART 1 is capable of processing arbitrary sequences of binary input patterns, while ART 2 is capable of handling either binary or analog input patterns. These ART modules are linked by a Map Field 130 and an internal controller (not shown) that ensures autonomous system operation in real time. The Map Field 130 controls the learning of an associative map from $ART_a$ recognition categories to $ART_b$ recognition categories, as well as matching tracking of the $ART_a$ vigilance parameter 140 (ρ'). The vigilance parameter 140 determines the closeness between the $ART_a$ recognition category and the $ART_b$ recognition category.

Figure 2:
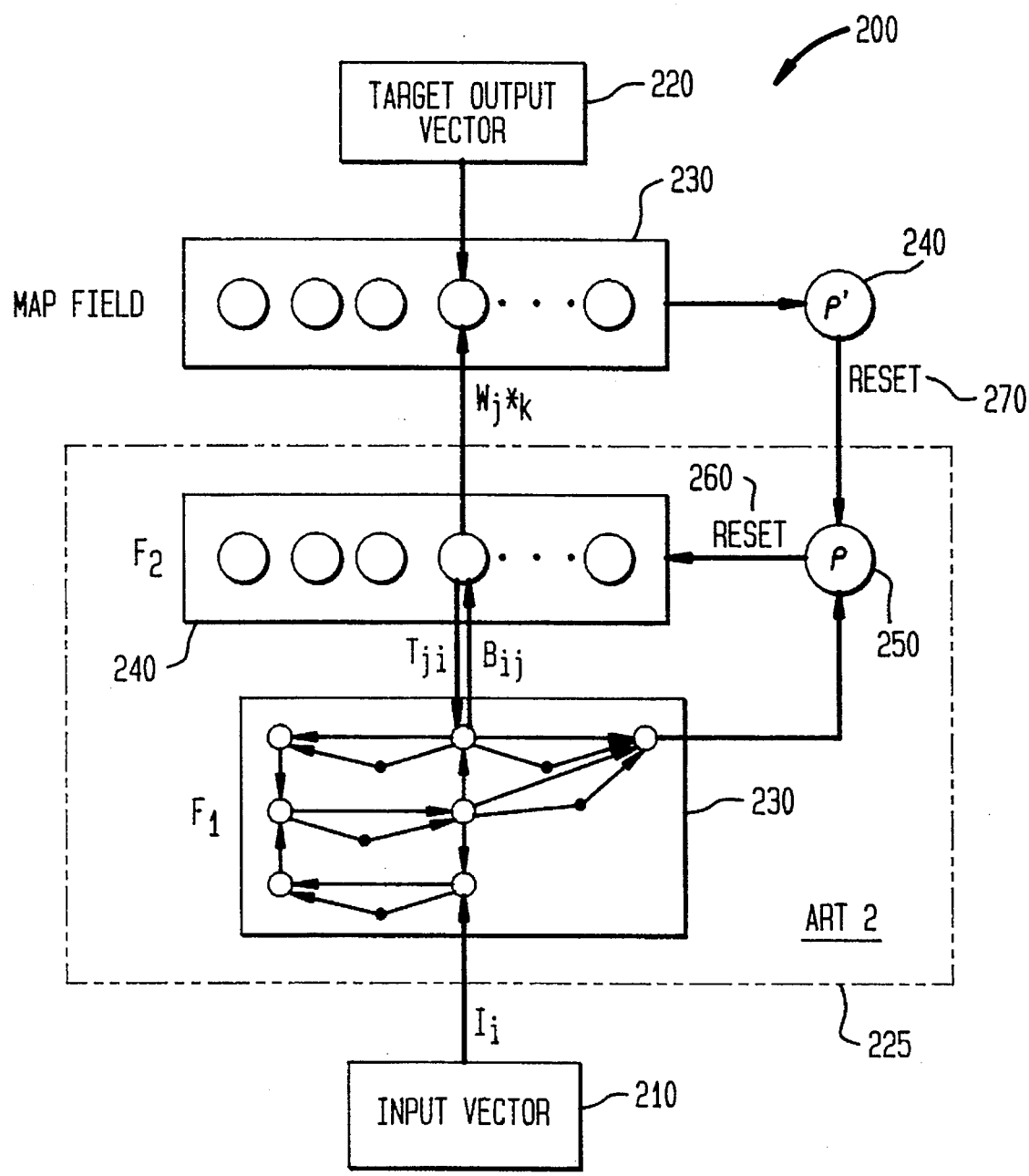
FIG. 2 illustrates a modified ARTMAP network adopted to perform supervised learning.

A neural network architecture and training method is disclosed that is a modification of an ARTMAP architecture. FIG. 2 illustrates a modified ARTMAP network 200. The modified ARTMAP network 200 is an efficient and robust paradigm which has the unique property of incremental learning. Unlike other popular neural networks, such as back propagation, the modified ARTMAP network 200 does not have to be trained with all the patterns, old and new, every time a new pattern is discovered.

The modified ARTMAP network 200 includes an ART module 225 that accepts an input pattern 210 (also referred to as input vector 210). An ART 2 neural network is used as the underlying ART module 225. The ART module 225 is connected to a map field 230 that accepts as an input a target output pattern 220 (also referred to as a target output vector 220). The map field 230 performs a mapping between a recognition category supplied by the ART module 225 and the target output pattern 220. The map field 230 also triggers a vigilance test 240 that determines the closeness between the recognition category and the target output pattern 220.

During the training of the modified ARTMAP network 200, both an input pattern 210 and a desired output pattern 220 are presented to the network 200. In a preferred embodiment, an input pattern 210 consists of two hundred (200) data points. The desired output pattern 220 is a binary vector, with each node of the vector corresponding to a particular machine condition. During the network testing phase, only the input pattern 210 is provided to the modified ARTMAP network 200.

2. Exponentially Weighted Moving Average

A. Theoretical Background and Modeling (a) Parametric Modeling Method

Figure 17:
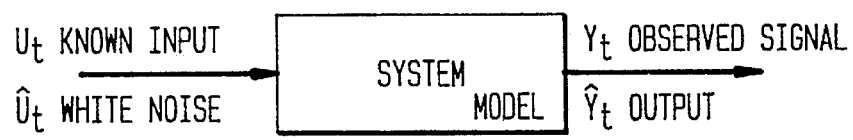
FIG. 17 illustrates a parametric modeling schematic that operates on incoming data or autocorrelation estimates.

Parametric modeling methods operate on incoming data or autocorrelation estimates to compute a set of parameters which correspond to an a priori model of the data statistic. This concept can be shown in FIG. 17, where the linear prediction of $Y_t$ is $$\hat{y}_t = a_1 y_{t-1} + a_2 y_{t-2} + \ldots a_p y_{t-p} \tag{1}$$

and p is the number of autoregressive parameters in the model.

(b) Autoregressive Process

An autoregressive process is represented by a difference equation of the form:

$$X(n) = \sum_{i=1}^{p} \phi_i X(n-i) + e(n) \tag{2}$$

where $X(n)$ is the real random sequence, $\phi_i$, i=1, . . . , p are parameters, and $e(n)$ is a sequence of independent and identically distributed zero-mean Gaussian random variables with constant variance, that is, $$E\{e(n)\} = 0 \tag{3}$$

$$E\{e(n)e(j)\} = \begin{cases} \sigma^2 N, & \text{for } n = j \\ 0 & \text{for } n \neq j \end{cases} \tag{4}$$

$$f_{e(n)}(\lambda) = \frac{1}{\sqrt{2\pi} \, \sigma_N} \exp\left\{ \frac{-\lambda^2}{2\sigma_N^2} \right\} \tag{5}$$

The sequence $e(n)$ is called white Gaussian noise. Thus, an autoregressive process is a linear difference equation model when the input or forcing function is white Gaussian noise (see Jangi, S., et al., "Embedding spectral analysis in equipment," *IEEE Spectrum*, February 1991, p. 42).

Thus, for a machine operating under normal conditions, the vibration condition of the machine can be described by an AR process where the values of e(n) are white Gaussian noise.

(c) Model Validation

Figure 18:
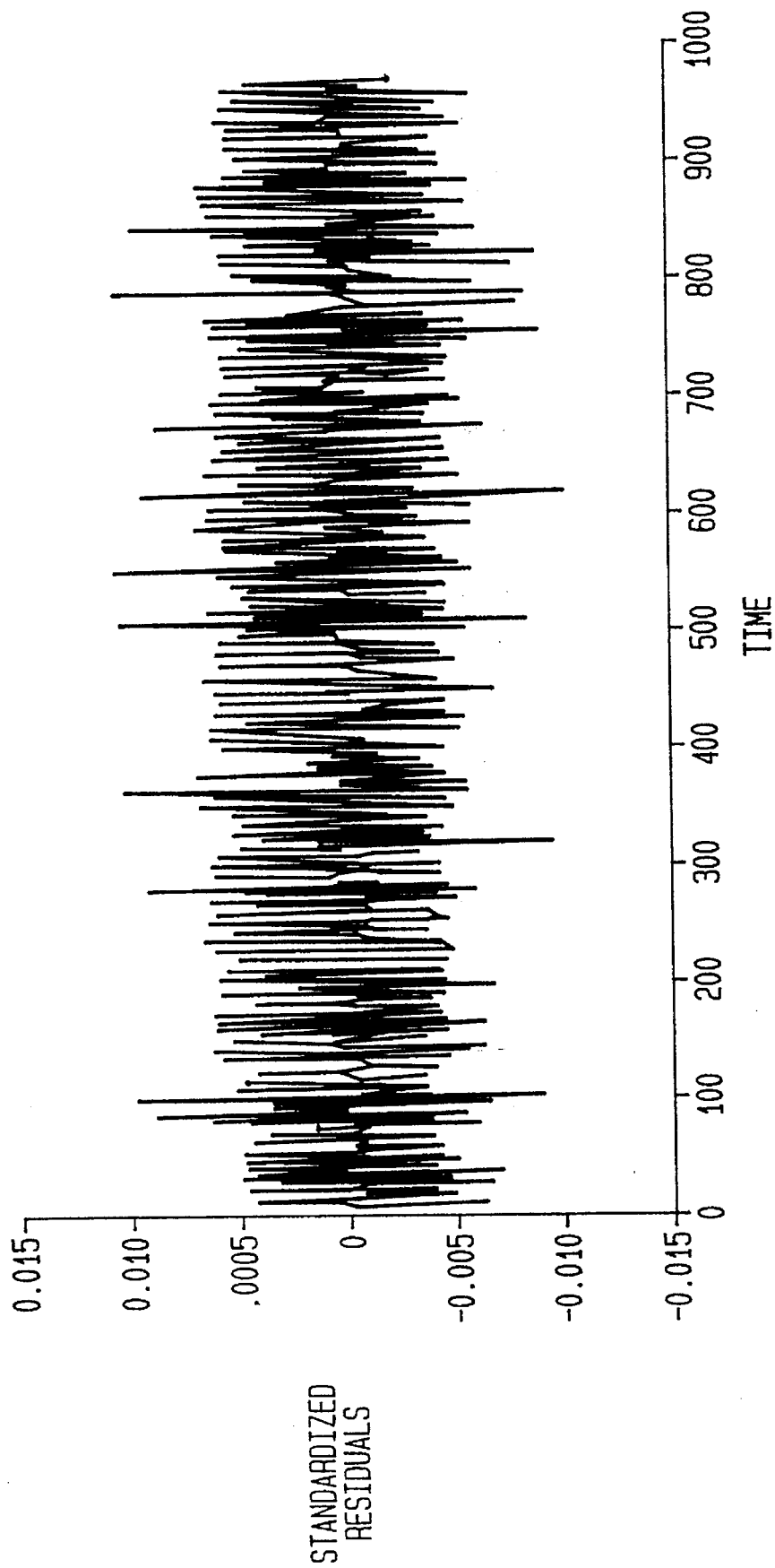
FIG. 18 illustrates a plot of the anticipated random distribution of residuals representing a normal machine condition.

If the model is suitable, the vibration signal will be defined to a large degree by the model and the deviations, or residuals, of the predicted signal from the actual signal for each point in time are distributed as whim Gaussian noise and, therefore, randomly distributed about the mean value zero. If the stochastic component is white noise and the trend in the vibration signal is adequately modeled, a plot of the residuals over time is expected to exhibit a rectangular scatter plot with no discernible pattern, meaning the variance is constant. This anticipated random distribution of the residuals is apparent in the plot of the residuals over time for a set of dam representing a normal machine condition, as shown in FIG. 18.

Gross nonnormality can be evaluated by plotting a histogram of the residuals. Since the errors are expected to be normally distributed, the histogram should closely resemble a normal distribution.

A final check for normality was conducted by calculating the normal scores of the residuals. The $t_{th}$ normal score is defined to be the $(t-3/8)/(n+1/4)$ percentage point of the standard normal distribution. With normally distributed data, a plot of the $t_{th}$ ordered data value (residual) versus the corresponding normal score should fall approximately on a straight line. This phenomenon occurs in the normal plot of a normal data set (see FIG. 3–4). Likewise, each of the other data sets showed an approximate straight line in the plot of the standardized residuals vs normal scores.

(d) Selecting AR Parameters

Determination of the AR parameters can be achieved by one of several techniques: Yule-walker method, Burg method, Covariance method, Modified Covariance method, etc. (see Marple, S., Digital Spectral Analysis with Applications, Prentice-Hall, Inc., 1987, pp. 224–231, 251). In a preferred embodiment, the modified covariance method is used since it eliminates problems encountered by using the other methods—frequency resolution, spectral line splitting, and bias of the frequency estimate (see Jangi, S., et at., "Embedding spectral analysis in equipment," *IEEE Spectrum*, February 1991, p. 42).

(e) Selecting AR Order

Criteria used for the selection of the AR model order were final prediction error (FPE), Akaike information criteria (AIC), and criterion autoregressive transfer (CAT) function.

FPE selects the order of the AR process so that the average error variance for a onestep prediction is minimized, where the error variance is the sum of the power in the unpredictable part of the process and a quantity representing the inaccuracies in estimating the AR parameters. The FPE for an AR process is defined as follows:

$$FPE[p] = \hat{\rho}_p \left( \frac{N+(p+1)}{N-(p+1)} \right) \quad (6)$$

where N is the number of data samples, p is the order, and $\hat{\rho}_p$ is the estimated white noise variance.

The AIC determines the model order by minimizing an information theoretic function. Assuming the process has Gaussian statistics, the AIC for an AR process has the following form:

$$AIC[p] = N \ln \hat{\rho}_p + 2p \quad (7)$$

A final criterion, CAT, selects the order p as that which minimizes the estimate of e difference between mean square errors of the true prediction error filter and the estimated filter. This difference is calculated from the following equation:

$$CAT[p] = \left( \frac{1}{n} \sum_{j=1}^{p} \overline{\rho}_j^{-1} \right) - \overline{\rho}_p^{-1} \quad (8)$$

where $\overline{\rho}_j = [N/(N-j)]\hat{\rho}_j$ and p is chosen to minimize CAT[p].

(f) Modified Covariance Method

The pth-order forward and backward linear prediction errors for the modified covariance method may be represented as the vector inner products $$e_p^f[n] = x_p^T[n] a_p^{fb}[n] \quad (9)$$

$$e_p^b[n] = x_p^T[n] J a_p^{fb}, \quad (10)$$

where the data vector $x_p[n]$ and linear prediction coefficient vector $a_p^{fb}$ are defined as follows:

$$x_p[n] = \begin{pmatrix} x[n] \\ x[n-1] \\ \vdots \\ x[n-p] \end{pmatrix}, a_p^{fb} = \begin{pmatrix} 1 \\ a_p[1] \\ \vdots \\ a_p[p] \end{pmatrix} \quad (11)$$

and J is a (p+1)×(p+1) reflection matrix. Based on measured data samples x[1], . . . , x[N], the modified covariance method minimizes the average of the forward and backward linear prediction squared errors.

$$\rho^{fb} = \frac{1}{2} \left[ \sum_{n=p+1}^{N} [|e_p^f[n]|^2 + |e_p^b[n]|^2] \right] \quad (12)$$

(g) Exponentially Weighted Moving Average (i) Control Statistic

The exponentially weighted moving average (EWMA) control statistic is defined as follows:

$$EWMA_t = max\{(1-\lambda)EWMA_{t-1} + \lambda \ln[\rho_{normalized}^{fb}], 0\} \quad (13)$$

where $EWMA_0 = 0$ $EWMA_t$=predicted EWMA value at time t (new EWMA)

$EWMA_{t-1}$=predicted EWMA value at time t-1 (old EWMA)

$\ln[\rho_{normalized}^{fb}]$ is the sample variance of observed values at time t $\lambda$ is a smoothing constant satisfying $0<\lambda \leq 1$ that determines the depth of memory of the EWMA (ii) Weighting Constant The EWMA can be written as:

$$y_{t+1} = \sum_{i=0}^{t} w_i y_i \quad (14)$$

where the $w_i$ are weights and $w_i = \lambda(1-\lambda)^{t-1}$.

The sum of the weights $$\sum_{i=0}^{t} w_i = 1.$$

The constant $\lambda$ determines the "memory" of the EWMA statistic. That is, $\lambda$ determines the rate of decay of the weights and in turn, the amount of information recollected from the past data. As $\lambda$ approaches 1, $w_1$ approaches 1 and $\hat{y}_{t+1}$ is nearly equivalent to the most recent observation $Y_t$. On the other hand, as $\lambda$ approaches 0, the most recent observation has small weight and previous observations nearly equal weights.

(iii) Upper Control Limit

The upper control limit for the EWMA statistic is $$UCL = \mu_p^{lb} + 4\sigma_p^{lb} \quad (15)$$

where $$\mu_p^{lb} = \frac{1}{n} \sum_{i=1}^{n} \mu_{p_i}^{lb} \quad (16)$$

$$\sigma_p^{lb} = \sqrt{\frac{1}{n-1} \sum_{i=1}^{n} \rho_i^{lb} - \mu_{p_i}^{lb}}, \quad (17)$$

and n= number of data sets initially collected under a normal machine condition.

(iv) EWMA Characteristics

The EWMA is a statistic with the characteristic that it gives less and less weight to data as it becomes older and older.

The EWMA chart was chosen since it has been proven superior to the range chart or $s^2$ in terms of its ability to quickly detect small percent increases in the process standard deviation (see Crowder, S., et at., *Journal of Quality Technology* 24(1):12–21 (1992)). In addition, the EWMA is easy to plot, easy to interpret, and its control limits are easy to obtain. A major advantage of employing EWMA is that it provides a mechanism for dynamic process control.

To control a process it is convenient to forecast where the process will be in the next instance of time. Then, if the forecast shows a future deviation from target that is too large, some electromechanical control system or process operator can take remedial action to compel the forecast to equal the target. In manufacturing, a forecast based on the unfolding historical record can be used to initiate a feedback control loop to adjust the process (see Box, G., et al., Statistic for Experimenters, John Wiley & Sons, New York, N.Y., 1978).

Lambda ($\lambda$) determines the "memory" of the EWMA statistic; that is, $\lambda$ determines the rate of decay of the weight and hence, the amount of information secured from the historical dam. The choice of 1 is somewhat arbitrary and was experimentally chosen to provide the smallest predicted variance (error) with a value of 0.7.

From Equation (13), it can be seen that the logarithmic scale is used. The meaningful presentation of vibration data is essential in order to enable a diagnostician to accurately determine the true condition of a machine. The use of a logarithmic scale provides a representation closer to the vibrational behavior of machines (see Archambault, R., "Getting More Out of Vibration Signals: using the Iogarithmic scale," *Proceedings of the 1st International Machinery Monitoring and Diagnostics Conference*, Las Vegas, Nev., 1989, pp. 567–571). It has been recommended that the log of the sample variances should be used when making inferences about variances of normally distributed data (see Box, G., et al., Statistic for Experimenters, John Wiley & Sons, New York, N.Y., 1978). One reason is that the logs of the sample variances will be much more normally distributed than the sample variances themselves. Also, the variance of $\ln(\rho^{lb})$ is independent of $s^2$ and depends only on the sample size n.

An increase in $s^2$ corresponds to an increase in the location parameter of the log-gamma distribution (the distribution of $\ln(\rho^{lb})$). Thus, an increase in the underlying process standard deviation should cause an increase in the mean level of the plotted EWMA values. Because of its simplicity and the properties listed above, the log transformation is considered to be an appropriate transformation.

Since vibration signals collected on rotating machinery can be very complex, as the vibration signal measured at a given point on the machine is the sum of all the internal forces applied to the machine modified by their respective transmission paths, the logarithmic scale provides a large range on which to display all the relevant data (see Archambault, R., "Getting More Out of Vibration Signals: using the logarithmic scale," *Proceedings of the 1st International Machinery Monitoring and Diagnostics Conference*, Las Vegas, Nev., 1989, pp. 567–571].

B. Detailed Operational Description

Figure 19:
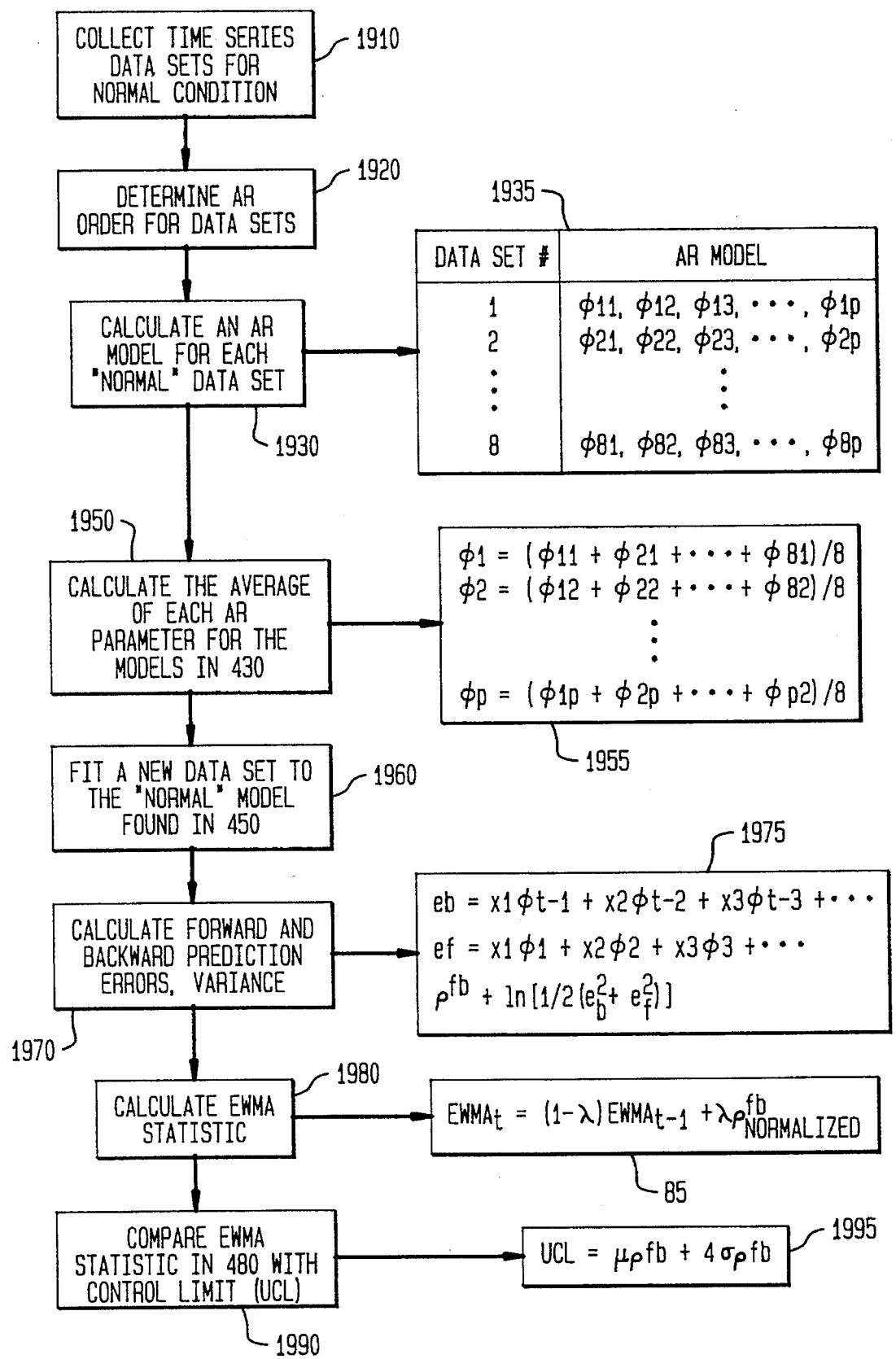
FIG. 19 is a detailed flowchart of the methodology used to calculate an EWMA in accordance with the present invention.

FIG. 19 is a detailed flowchart of the methodology used to calculate the EWMA in accordance with the present invention. That is, it outlines a methodology for monitoring and diagnosing a machine condition. Initially, time series data (e.g., vibration signals) is collected from a physical machine (in a lab setup) under normal machine conditions, as shown in block 1910. In a preferred embodiment, each of the data sets consists of 1000 data points. Note that the present invention is not limited to machine conditions, and can be extended to processes as well as would be apparent to a person skilled in the relevant art.

Data collection is conducted using the following setup: a DC motor connected to a shaft by a drive belt, two cylindrical pillow block bearings mounted on each end of the shaft and secured to a steel plate, an oscilloscope to display the raw vibration signal collected, an amplifier to magnify the signal, and a DT2821-G-8DI data acquisition board. Vibration signals were collected from the bearing using 328CO4 PCB accelerometers mounted on the bearing housing.

Figure 20:
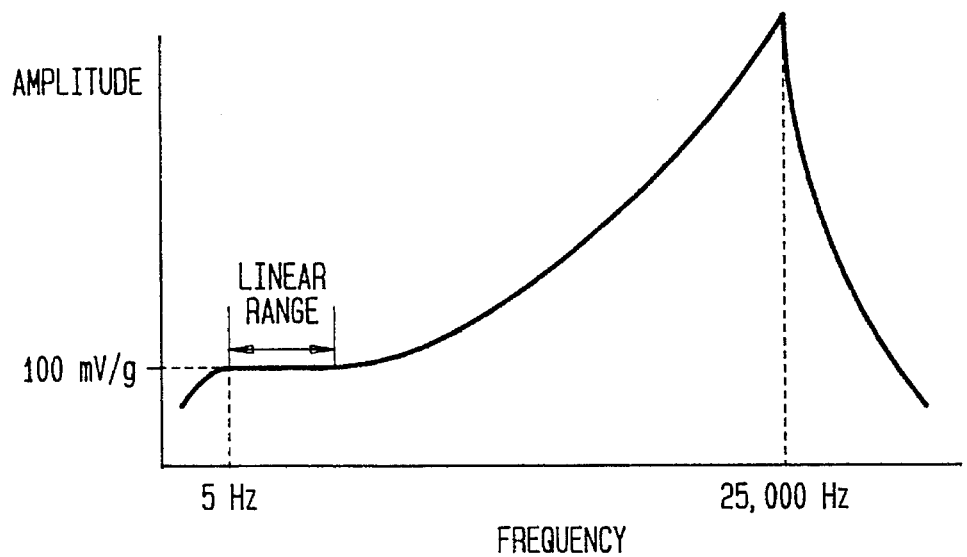
FIG. 20 displays the sensitivity response (amplitude) of an accelerometer versus frequencies.

Accelerometers are transducers whose voltage output is proportional to acceleration or, as a more useful description, the internal forces in the machine. If the acceleration level is high, then the internal forces are high. Forces are the cause of oscillation, in addition to excessive wear and premature failure. The sensitivity response (amplitude) of an accelerometer versus frequencies is displayed in FIG. 20.

Accelerometers are the preferred transducers in machine condition monitoring due to the following reasons: extreme ruggedness, large frequency response, large dynamic range—accelerometers can detect very small vibrations without being damaged by large vibrations, output is proportional to forces which are the cause of internal damage, and high-frequency sensitivity for detecting bearing faults.

Next, an appropriate AR model (i.e., one that adequately describes the vibration data being collected) is selected using the criteria defined in Equations (6), (7), and (8). As shown in block 1920, a suitable AR order is then chosen. After choosing a suitable AR order for the normal condition, an AR model is generated for each of the data sets collected under the normal machine condition, i.e., first order parameters ($\phi_{i1}$), second order parameters ($\phi_{i2}$), up to p order parameters ($\phi_{ip}$) for i=1, 2, . . . , n data sets, as shown in blocks 1930 and 1935.

As shown in blocks 1950 and 1955, an average value is calculated for the first order AR parameter through the pth order AR parameter from the AR models generated in blocks 1930 and 1935. This calculation is performed in order to define a model that would be representative of a normal machine condition under the conditions defined in the lab setup.

Once the model is established for the normal machine condition, new data is collected for an abnormal machine condition. Then the abnormal vibration signals are fit to the "normal" model found in block 1950 and 1955 as an indicator of how closely the normal model fits the data set collected under the current condition. This step is represented in block 1960.

In order to measure the fit of the data to the normal model, forward and backward prediction errors are calculated to determine the $\rho_{normalized}^{fb}$ value of the data, as shown in blocks 1970 and 1975. This process is described above in Section 2(A)(f) (i.e., modified covariance method). The normalization is based on the normal machine condition since the purpose of the present invention is to be able to detect any deviations from the normal machine condition. Normalization is utilized to uncover all possible collections or sets containing the same data and allows current and previous data for a machine to be superimposed, regardless of the operating speed. In addition, normalization allows the creation of an average data file for each specific machine type.

Vibration signatures for many identical machines taken at different times at slightly different operating speeds can be accumulated statistically and represented by a single set of averaged narrow band spectra (see Watts, W., et al., "A Portable, Automated Machine Condition Diagnostics Program Using Order Normalized Vibration Data," *Proceedings of the 1st International Machinery Monitoring and Diagnostics Conference*, Las Vegas, Nev., 1989, pp. 637–643). To determine whether the vibration signature of a machine is significant, the current condition is compared to the normal condition through the $\rho^{fb}$ values.

Given the $\rho^{fb}$ value found in blocks 1970 and 1975, an exponentially weighted moving average (EWMA) statistic is calculated, with $\lambda=0.7$, as shown in block 1980. The calculated EWMA statistic is an indicator of the overall machine condition and is compared to the upper control limit (UCL) (describe above in section 2(G)(iii)) to determine if the machine is in a state of control or if it is out-of-control. This step is shown in blocks 1990 and 1995. If the EWMA value exceeds the UCL, this is a signal that an abnormal machine condition exists and action should be taken.

C. Data Analysis

The following description is the result of applying the above described invention to an actual machine in a lab setting. Although different dam sets will result in a slightly different outcome, the principles and methodology described herein remain the same. After collecting data from the machine, the modified covariance method and the three methods described above are used to determine the appropriate AR model to adequately describe the normal machine condition. In a preferred embodiment, the most suitable order for the AR model is 33, resulting in a ratio of AR order to sequence length (1000) of 0.033. The value is preferably small since frequency bias and line splitting increase with an increasing ratio of AR order to sequence length.

In a preferred embodiment, once the normal model is established for the normal condition, vibration data is collected under three abnormal operating conditions, namely misaligned shaft, loose bearing, and contaminated bearing.

For each data set collected under one of the four conditions, the minimum and maximum variances were determined, as shown in Table 1. These variances were normalized by dividing the variance by the average variance under a normal condition (0.0000048582) and taking the natural log of the variance for both the minimum and maximum variances for each machine condition. The variance values were used to determine the upper and lower bounds of the EWMA, as shown in Table 2.

The numbers in the upper portion of each cell in Table 2 represent the minimum and maximum observed EWMA statistic based on actual dam collected in the lab. The numbers in the lower portion of the cell are based on statistics of the collected data and were calculated using $\mu_{\rho^{fb}} - 4\sigma_{\rho^{fb}}$ for the lower bound and $\mu_{\rho^{fb}} - 4\sigma_{\rho^{fb}}$ for the upper bound, where $\mu_{\rho^{fb}}$ is the average value for the EWMA statistic for each machine condition, i.e., $$\mu_p^{fb} = \frac{1}{n}\left[\sum_{i=1}^{n} \rho_i^{fb}\right],$$

where n is the number of samples collected.

The standard deviation, as well as $\mu_{\rho^{fb}}$, was determined for each bearing condition. Standard deviations are calculated by the following formula:

$$\sigma_p^{fb} = \sqrt{\frac{1}{n}\left[\sum_{i=1}^{n}(\rho_i^{fb} - \mu_p^{fb})^2\right]} \tag{18}$$

In Table 2, the upper and lower bound of EWMA values for the abnormal conditions (misalignment, contamination, and looseness) are calculated based on the minimum and maximum EWMA statistic calculated for the normal condition and the variances of the abnormal conditions in Table 1. For example, under the normal condition, the minimum and maximum EWMA values for all eight data sets collected was 0.000000 and 0.126535, consecutively. Referring to Equation (13), the EWMA statistic is calculated by $$EWMA_t = \max\{(1-\lambda)EWMA_{t-1} + \lambda ln \rho_{normalized,t}^{fb}, 0\}$$

TABLE 1

Calculated "Normalized" Variances for a Normal Machine Condition and Three Abnormal Machine Conditions

| | Statistic | |
|---|---|---|
| Condition | Average value $\mu_{\rho^{fb}}$ | Standard deviation $\sigma_{\rho^{fb}}$ |
| normal | 0.100081 | 0.124959 |
| misalignment | 2.561171 | 0.116305 |
| contamination | 5.002439 | 0.302079 |
| looseness | 3.449739 | 0.125359 |

Under a misalignment condition, for example, the minimum EWMA statistic that could occur is calculated using the minimum variance found under a misalignment condition and the minimum EWMA statistic for the normal condition. Similarly, the maximum EWMA statistic that could occur is calculated using the maximum variance found under a misalignment condition and the maximum EWMA statistic for the normal condition.

TABLE 2

Calculated EWMA Statistics for a Normal Machine Condition and Three Abnormal Machine Conditions

| | EWMA Statistic: | |
|---|---|---|
| Condition | Lower Bound | Upper Bound |
| normal | 0.000000 | 0.134323 |
| | (0.000000) | (0.496657) |
| misalignment | 1.165905 | 1.315764 |
| | (1.072859) | (1.501256) |
| contamination | 2.283083 | 2.487441 |
| | (2.209966) | (2.709934) |
| looseness | 1.835429 | 1.975226 |
| | (1.740603) | (2.162600) |

TABLE 3

Calculated Statistics of EWMA Values for a Normal Machine Condition and Three Abnormal Machine Conditions

| Condition | Statistic | |
|---|---|---|
| | Minimum EWMA | Maximum EWMA |
| Normal | 0.0000 | 0.4967 |
| Misalignment | 1.0729 | 1.5013 |
| Contamination | 2.2020 | 2.7099 |
| Looseness | 1.7406 | 2.1626 |

Specific calculation that were performed to derive the numbers in Tables 1–3 can be found in Spoerre, J. K., "Machine Performance Monitoring and Fault Classification Using an Exponentially Moving Average Scheme," Masters Thesis, The University of Iowa, May 1993.

Figure 21:
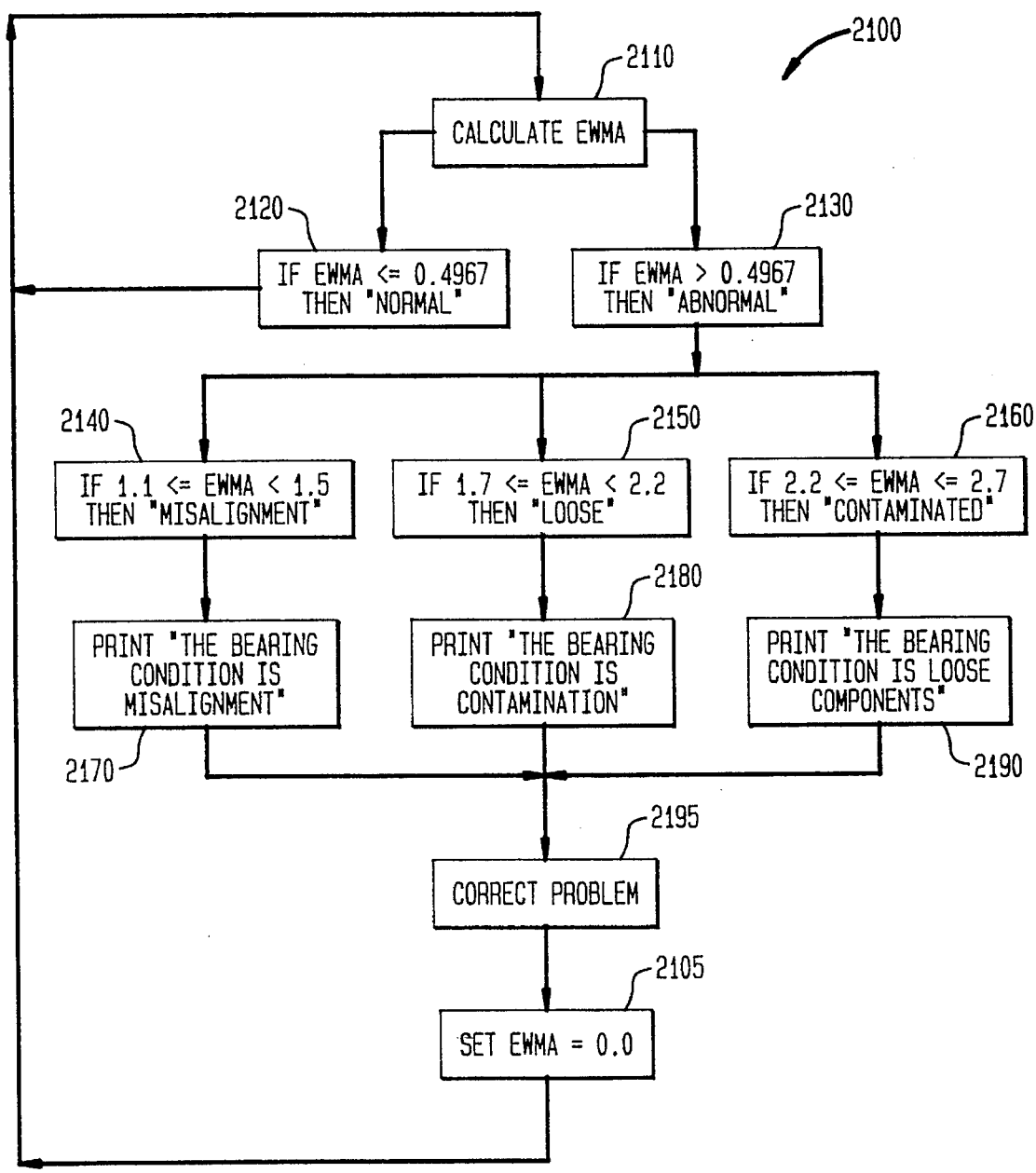
FIG. 21 is a flowchart of a diagnosis and monitoring procedure that utilizes an exponentially weighted moving average.

The range of values for each of the operating conditions given above were well-defined with no overlap among different machine conditions. FIG. 21 illustrates a diagnosis and monitoring procedure that uses the EWMA technology. Initially, the EWMA statistic is set to 0.0, as shown in block 2105. Then, using the procedure outlined above, the EWMA statistic is calculated, as shown in block 2110. Next, the EWMA statistic is checked against a "normal condition" upper limit, which in the example given above is 0.4967.

If the EWMA statistic falls below this upper limit then the machine is operating normally, as shown in block 2120. In this scenario the procedure flows back to block 2110. However, if the EWMA statistic falls above the upper limit then a potential abnormal condition exists, as shown in block 2130. Based on table 2, blocks 2140, 2150, and 2160, each indicate a different abnormal condition. Namely, if the EWMA statistic falls between 1.1 and 1.5 then the abnormal condition is misalignment; if the EWMA statistic falls between 1.7 and 2.2 then the abnormal condition is loose bearings; and if the EWMA statistic falls between 2.2 and 2.7 then the abnormal condition is contamination. Of course other abnormal conditions can be detected by following the above procedure and determining the appropriate EWMA statistic.

Once the abnormal condition is detected, the procedure 2100 prints via the user interface 150 the detected fault, as shown in blocks 2170, 2180, and 2190. At this time, an operator corrects the problem with the machine, as shown in block 2195, and the EWMA statistic reset to 0.0 (i.e., normal condition).

Figure 22:
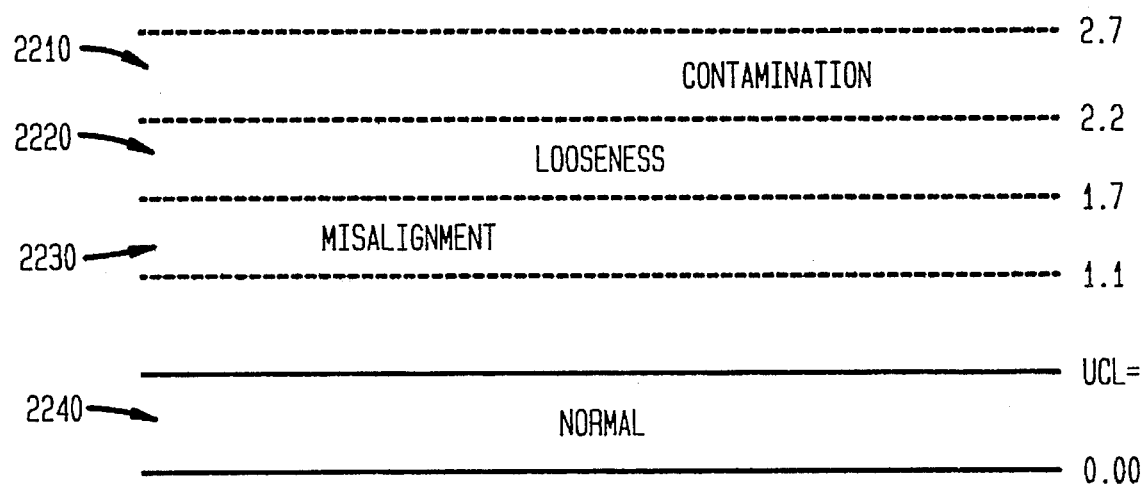
FIG. 22 is an EWMA chart that illustrates three abnormal conditions.

FIG. 22 illustrates an EWMA chart. The EWMA chart can be divided into bands 2210–2240 that represent the location of specific machine conditions. A normal condition is shown in band 2240, while the abnormal machine conditions are shown in bands 2210–2230.

By developing an AR paramatric model to characterize the normal machine condition, the EWMA control statistic is able to identify whether the machine is in a normal state ("in control") or in an abnormal state ("out of control"). As an abnormal bearing condition begins and worsens, the plot on the EWMA control chart is near the control limit and shows a trend towards the limit; eventually the EWMA control statistic extends well beyond the control limit if the abnormal condition is not corrected.

It has also been determined that there is a positive correlation between the average amplitude of the signal and the average EWMA statistic for a given machine condition. As the average amplitude increases, the EWMA value increases. This implies that the EWMA statistic is sensitive to changes in amplitude. Since an increase in amplitude occurs when a bearing or other machine component undergoes the initial stages of failure, the EWMA technique has the ability to detect small changes in amplitude once a defect occurs.

Furthermore, it has been shown that the deviation of the variance at time t from the variance established under a normal condition is an indicator of current bearing condition. If this deviation is nearly zero, the bearing is operating in a normal condition; however, if this value is significantly different from zero, an out of coil state exists and corrective action is necessary.

3. Parametric Modeling and ART 2 Approach

Figure 3:
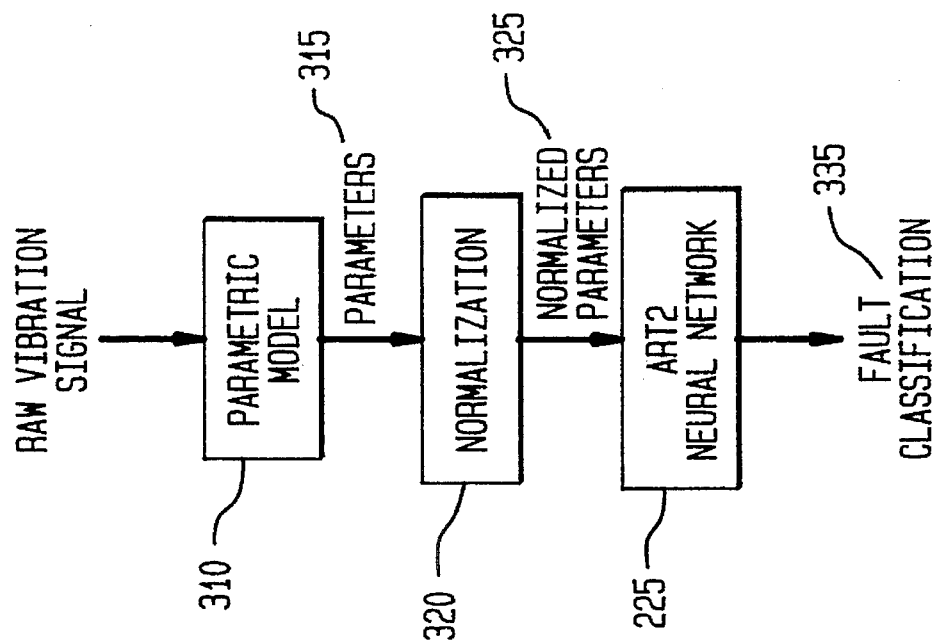
FIG. 3 shows a framework that illustrates the three phases of the present invention.

FIG. 3 shows the framework of the present invention. It comprises three modules: a parametric model 310, a normalization process 320, and an ART 2 neural network 225. In a preferred embodiment, an autoregressive (AR) parametric model is used in combination with the ART 2 neural network 225. However, an autoregressive moving average (ARMA) model can also be used. Both AR models and ARMA models are known in the art.

The parametric model 310 is used to fit (i.e., mathematically describe) a raw vibration signal collected from a physical machine or process under review. After fitting the parametric model 310 to the vibration signal, a set of parameters 315 can be obtained. At this point, however, the parameters 315 cannot be fed into the ART 2 network 225 without pre-processing because they contain meaningful negative values which the ART 2 network 225 is not able to recognize. Therefore, a normalization process 320 has to be applied in order to ensure that the ART 2 network 225 can perform correctly with proper inputs.

Figure 16:
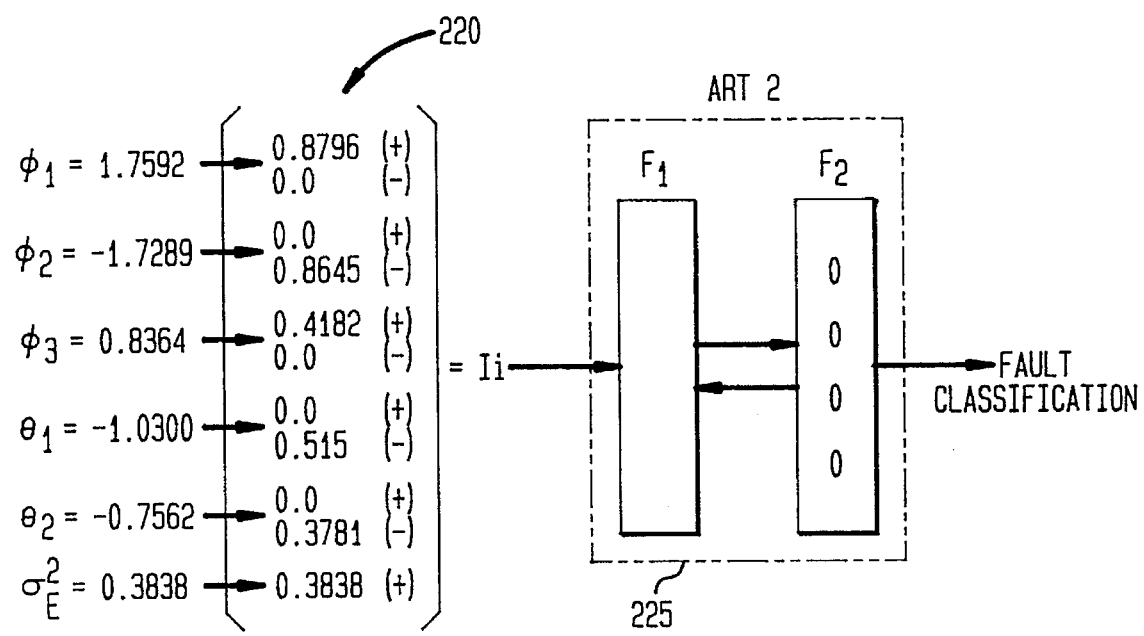
FIG. 16 shows an ART2 network with an example input vector.

The normalization process 320 requires two steps. First, each parameter 315 is divided into two parts: positive and negative. If a parameter 315 has a positive value, then the negative part will be assigned to zero, and vice versa. Secondly, scaling of the parameters 315 occurs by dividing each parameter 315 by the maximum parameter value. The residuals variance will only contain the positive part because its value is always positive. However, the variance needs to be divided by the maximum residuals variance. As such, an ARMA or AR model with n parameters will require $2n+1$ input nodes in the ART 2 input layer. For example, an ART 2 network 225 for an ARMA (3, 2) model (n=5) will require 11 input nodes. The input vector to the ART 2 network 225 for the ARMA (3, 2) model with the following parameters and residual variance is shown in FIG. 16.

$\Phi_1 = 1.7592$ $\Phi_2 = 1.7289$ $\Phi_3 = 0.8364$ $\theta_1 = -1.0300$ $\theta_2 = -0.7562$ $\sigma_E = 0.3838$ Suppose the maximum parameter value for both the positive and negative part is equal to 2 and the maximum residuals variance is equal to 1. Take $\Phi_1$ for example, the negative part is set to 0 because its value is positive. The positive part is divided by the maximum parameter value, 2, and a value of 0.8796 is obtained. For the residual variance, the value remains the same because the maximum residual variance is 1.

During training of the network, the ART 2 network 225 is presented with an input pattern, i.e., the normalized parameters 325. As a result, the network self-organizes fault classifications until it runs out of input patterns. At last, the final top-down weights ($T_{ji}$) and bottom-up weights ($B_{ij}$)

will be saved for later diagnostic use. During diagnosis of a fault, each input pattern is presented to the ART 2 network 225. Each node in the $F_2$ layer 240 represents a particular fault classification. The node in the $F_2$ layer 240 which passes the vigilance test 250 will be the output 335 of the ART 2 network 225.

As mentioned earlier, during the training of the modified ARTMAP network 200, both the input pattern 210 and the desired output pattern 220 have to be presented to the modified ARTMAP network 200. Each set of input patterns 210 and desired output patterns 220 is used to train the modified ARTMAP network 200 independently, which means that the modified ARTMAP network 200 can be trained incrementally. In a preferred embodiment, an input pattern 210 consisted of 200 data points of the vibration spectrum. The desired output pattern 220 is a binary vector, with each node of the vector corresponding to a particular machine condition.

4. Fault Diagnostics: Methodology and Implementation

This section describes the fault diagnostic system 400 developed in accordance with the present invention. The methodologies used in this system are covered throughout this section. Section 4.1 introduces the application of the autoregressive modeling technique for data preprocessing. Section 4.2 discusses the development of the fault diagnostic network. In Section 4.3, physical bearing models and a fuzzy logic-based hypothesis and test procedure for unknown patterns are presented.

4.1. Autoregressive (AR) Model

An autoregressive (AR) technique is a method of transferring signals from a time domain, the way they were captured through a set of sensors connected to a physical machine or process, to a frequency domain. Traditionally this is done with Fourier Transforms.

The benefit of using a parametric model for signal processing is that it can dramatically reduce the amount of data and still preserve the important characteristics of the signal. As a result of data reduction, the diagnosis and training time of a neural network will be greatly reduced. Since the training time increases about 10 times and the diagnosis time increases about 6 times when the number of input data increases from 200 to 2400, data reduction is critical, especially when multiple sensors are used in a real-time mode since the amount of data involved is increased. The present invention implements an AR model for on line signal processing. The mathematical form of an AR model is given in Equation 19.

$$X_t = \Phi_1 X_{t-1} + \Phi_2 X_{t-2} + \ldots + \Phi_p X_{t-p} + E_t \quad (19)$$

where $X_t$=time series, $\Phi_i$=the AR parameters, p=the order of AR model, $E_t$=residuals with NID (0, $\sigma_E^2$).

The order of the AR model is to be determined with an approach described in Lin, C.C., "Classification of Autoregressive Spectral Estimated Signal Patterns Using an Adaptive Resonance Theory (ART)," Master's Thesis, Department of Industrial Engineering, The University of Iowa, Iowa City, Iowa, 1992. It selects the order with the highest final prediction error (FPE) and Akaike information criterion (AIC) level. The equations of FPE and AIC are given by the following:

$$FPE(p) = \hat{\sigma}_p^2 \left( \frac{N + (p+1)}{N - (p+1)} \right) \quad (20)$$

$$AIC(p) = N\ln(\hat{\sigma}_p^2) + p\ln(N) \quad (21)$$

where N is the number of data samples, p is the AR order, and $\hat{\sigma}_p^2$ is the estimated linear prediction error variance at order p. Once the AR order is determined, it is fixed and then the AR model can be fitted to the sensory data to generate an AR parameter 315. Once normalized (as described above), the AR parameter 315 can be used as an input to the modified ARTMAP network 200.

4.2. Fault Diagnostic Network

The objective of using a fault diagnostic network (i.e., a modified ARTMAP network) is to provide rapid and accurate diagnosis of machine faults. The modified ARTMAP network 200 is an efficient and robust paradigm which has the unique property of incremental learning. Unlike other popular neural networks, such as back propagation, the modified ARTMAP network 200 does not have to be trained with all the patterns, old and new, every time a new pattern is discovered. The mechanics of the modified ARTMAP 200 is described in the following section.

4.2.1. Modified ARTMAP Network

The modified ARTMAP neural network 200 is an extension of the ART (Adaptive Resonance Theory) network which autonomously learns to classify arbitrarily ordered vectors into recognition categories based on predictive success. As described above with reference to FIG. 1, the ARTMAP neural network 100 is an unsupervised learning system built from a pair of ART modules 110, 120 that each produce a recognition category, and a Map Field 130 which controls the mapping between the pair of recognition categories.

In a preferred embodiment, the ARTMAP neural network only uses one input pattern (i.e., AR parameters). As such, a modification to the ARTMAP network shown in FIG. 1 is made in order to perform supervised learning. FIG. 2 shows a modified ARTMAP network 200, in which the second ART module is replaced by a target output 220. The target output 220 is provided by a user. An ART 2 neural network architecture 225 is chosen as the underlying ART module to handle analog input patterns (e.g., AR parameters).

Specifically, the ART 2 neural network architecture is used in a preferred embodiment since vibration or sound signals are used as an input to the modified ARTMAP neural network 200 and the energy level in a vibration or sound signal is a continuous analog signal. However, as would be apparent to those skilled in the art, signals other than sound signals can be applied to the modified ARTMAP neural network 200. Furthermore, the present invention can also be used with an ART 1 neural network architecture if arbitrary sequences of binary input patterns are used as an input to the modified ARTMAP neural network 200.

In the modified ARTMAP network 200, the ART2 network 120 has two layers: $F_1$ 230 and $F_2$ 240. Referring to FIG. 4, the $F_1$ layer 230 of the ART 2 network includes three processing levels and several gain control systems which enable the network to separate signal from noise and enhance the contrast of activation signals. Generally, each level performs two computations: integration of intrafield and interfield inputs to that level which produces an integrated activation signal and normalization of the integrated activation signal. The filled circles are the gain control systems which normalize the integrated activation signals.

Figure 5A:
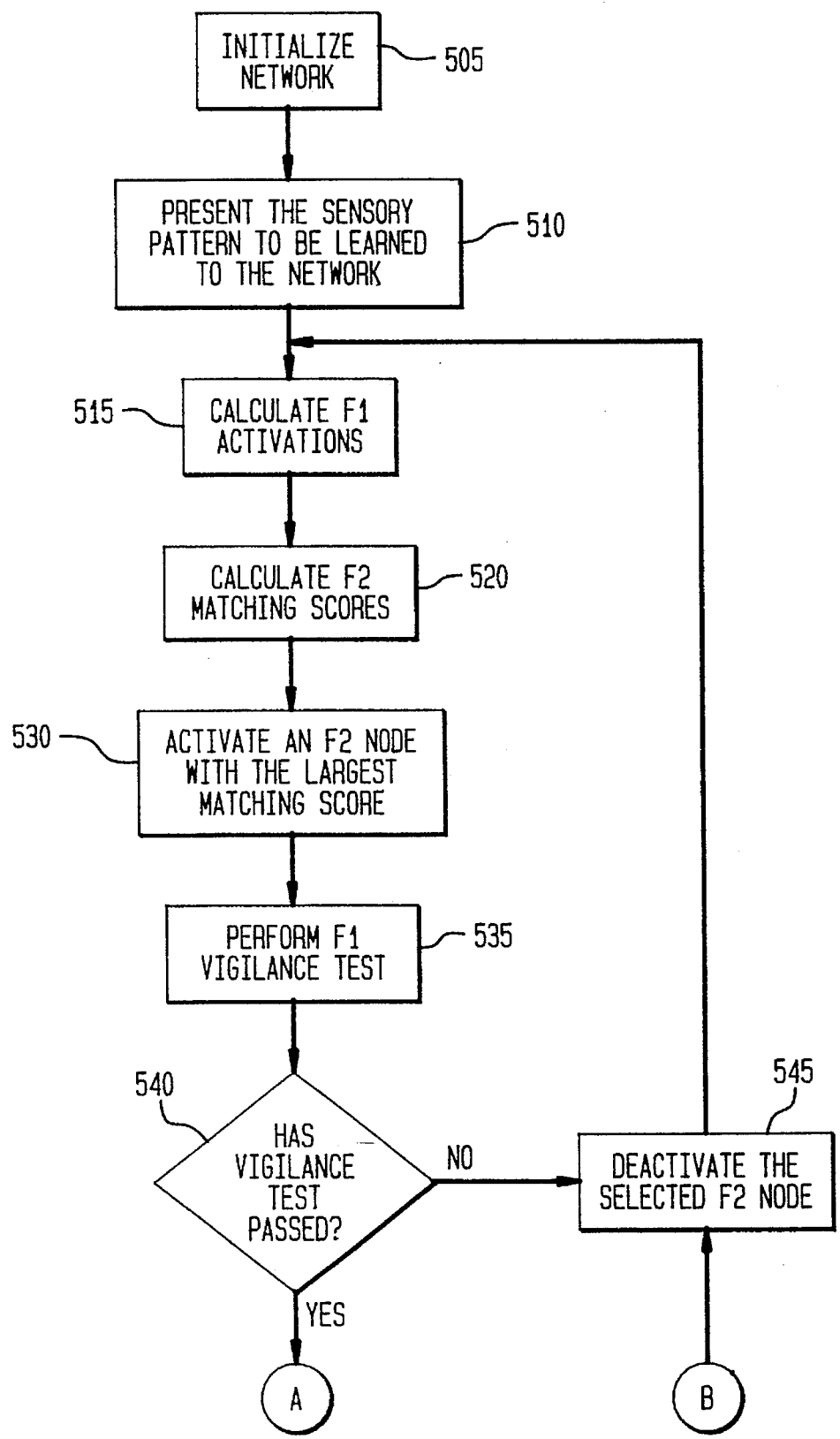
FIGS. 5a and 5b shows a flowchart of a training procedure for the modified ARTMAP network.
Figure 5B:
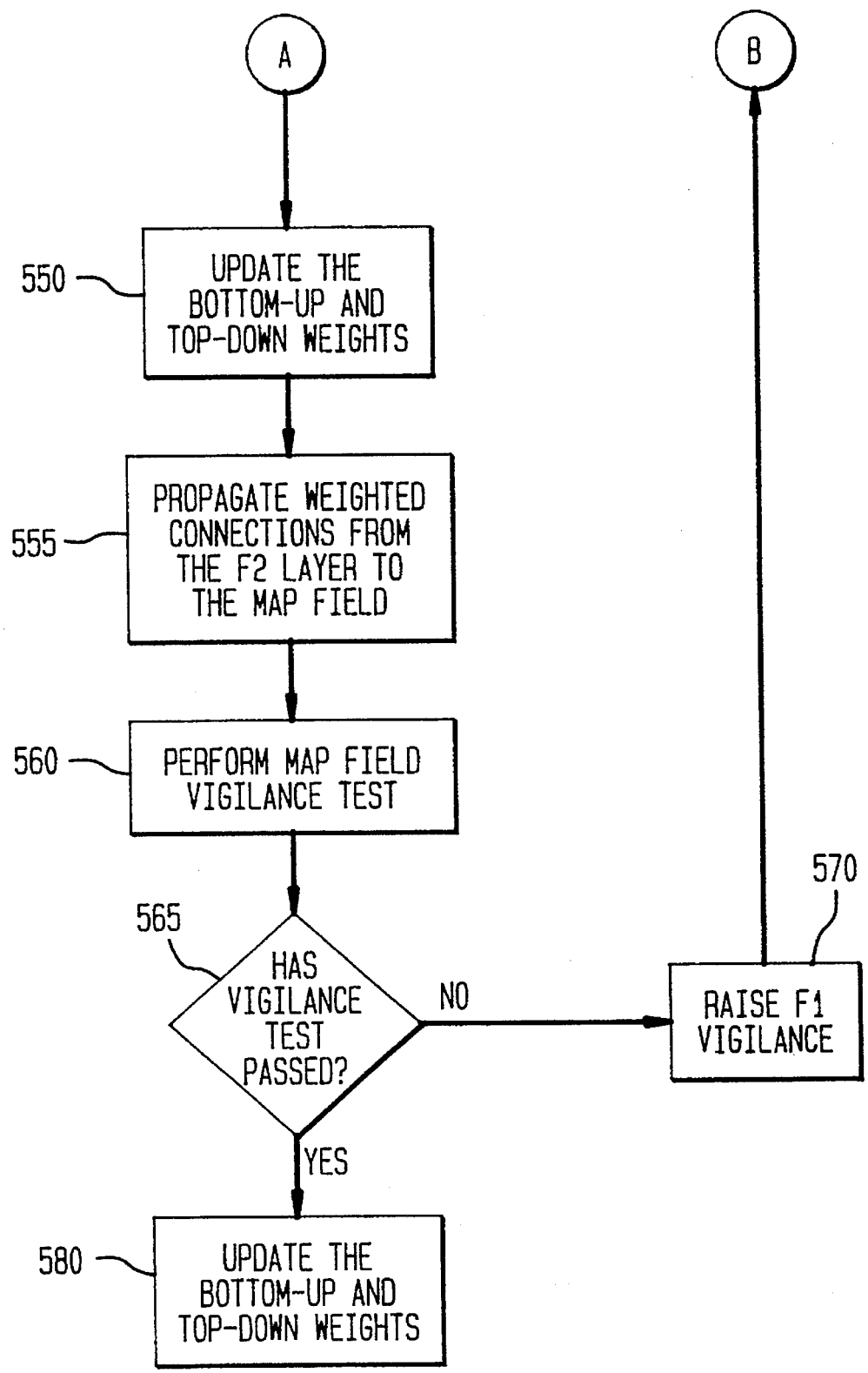

Training of the modified network is described below with reference to FIG. 4 and FIG. 5. FIG. 5 illustrates a flowchart of the procedure used to train the modified ARTMAP network 200.

As shown in block 505, before initiating training of the modified ARTMAP neural network 200, the following parameters are initialized:

$$T_{ji} = 0 \tag{22}$$

$$B_{ij} = \frac{1}{0.2 * \sqrt{N}} \tag{23}$$

$0 \leq i \leq N-1$, where N is the dimension of the input vector 210;

$0 \leq j \leq M-1$, where M is the number of $F_2$ nodes;

$w_i = x_i = v_i = u_i = q_i = p_i = 0$; and

Set a, b, c, d, e, θ, and ρ.

As shown in block 510, an input pattern to be learned is presented to the modified ARTMAP network 200. Next, the activation signals between the different nodes of the F1 layer 230 are generated, as shown in block 5 15. At the lower level of the $F_1$ layer 230, vector $w_i$ is the integration of an intrafield input vector $I_i$ and the interfield feedback signal $au_i$, i.e., $$w_i = I_i + au_i \tag{24}$$

where i is the ith node at the $F_i$ layer 230 and a is a constant. Once the vector $w_i$ is obtained, then it can be normalized to yield $x_i$ by the following equation:

$$x_i = \frac{w_i}{e + \|w\|} \tag{25}$$

where e is a constant close to zero and $\|w\|$ denotes the $L_2$ norm of a vector w.

The rest of activities in the $F_1$ layer 230 can be calculated according to the following equations:

$$v_i = f(x_i) + bf(q_i) \tag{26}$$

$$u_i = \frac{v_i}{e + \|v\|} \tag{27}$$

$$q_i = \frac{p_i}{e + \|p\|} \tag{28}$$

$$p_i = u_i + \sum_j g(j) T_{ji} \tag{29}$$

where b is a constant, g(j) is the activation of the jth node in the $F_2$ layer 240, and $T_{ji}$ is the top-down weight between the jth node in the $F_2$ layer 240 and the ith node in the $F_1$ layer 230. The linear signal function f in Equation (26) is $$f(x) = \begin{cases} 0 & \text{if } 0 \leq x < \theta \\ x & \text{if } x \geq \theta \end{cases} \tag{30}$$

where θ is a threshold value.

As shown in block 520, once the nodes in the $F_2$ layer 240 receive an input signal from the $F_1$ layer 230 (via bottom-up weight $B_{ij}$), the matching score for the nodes in the $F_2$ layer 240 is then computed according to the following:

$$\mu_j = \sum_i p_i B_{ij} \tag{31}$$

where $B_{ij}$ are the bottom-up weights.

Then, as shown in block 530, the node in the $F_2$ layer 240 with the largest matching score is activated. The activation of the $F_2$ layer 240 is given below:

$$g(j) = \begin{cases} d & \text{if the } j\text{th } F_2 \text{ node is active} \\ 0 & \text{otherwise} \end{cases} \tag{32}$$

where d is a constant between 0 and 1.

At this point, the $F_2$ layer 240 activation is propagated back to the $F_1$ layer 230. Next, as shown in block 535, the vigilance test 250 is carried out to determine whether the top-down signal matches the input pattern 210. The vigilance test 250 is given as follows:

$$r_i = \frac{u_i + cp_i}{e + \|u\| + \|cp\|} \tag{33}$$

$$\frac{p}{e + |r|} > 1? \tag{34}$$

where c is a constant and $0 < p < 1$. If the match fails to pass the vigilance test 250, then a reset 260 is sent to $F_2$ 240 which forces $F_2$ 240 to deactivate the selected node in the $F_2$ layer and search for the next best match, as shown in block 545. Otherwise, the bottom-up ($B_{ij}$) and top-down weights ($T_{ji}$) are adapted from the following equations:

$$B_{ij*}(t+1) = d[p_i - B_{ij*}(t)] \tag{35}$$

$$T_{j*i}(t+1) = d[p_i - T_{j*i}(t)] \tag{36}$$

where j* is the selected node in the $F_2$ layer 240. The step of updating the bottom-up weights and the top-down weights if the vigilance test passes is shown in block 550.

Once the ART module 120 is presented with an input vector 210, it selects a node in the $F_2$ layer 240 which passes the vigilance test 250. Then, the $F_2$ layer 240 activations are propagated to the Map Field 130 through the weighted connections ($w_{jk}$) between the $F_2$ layer 240 and the Map Field 130, as shown in block 555. The signals received from the $F_2$ layer 240 are calculated by the following equation:

$$X = \omega_{j*} \tag{37}$$

At the map field 130, a second vigilance test 140 is performed to determine the level of match between the predicted output from the $F_2$ layer 240 (X) and the target output pattern 220 (Y), as shown in block 560. A mismatch between X and Y will trigger a map field reset 270 to the underlying ART module 120. This occurs whenever the following condition holds:

$$\frac{\|X\|}{\|Y\|} < p' \tag{38}$$

where p' denotes the associative memory vigilance parameter 240. If the map field reset 270 occurs, the vigilance 250 of the underlying ART module 120 is raised to prevent the system 200 from making repeated errors, as shown in block 570. At this point, a reset 260 is sent to the $F_2$ layer 240 and forces the $F_2$ layer 240 to find the next best match, as shown in block 545. This process will continue until the second vigilance test 140 succeeds. Once the second vigilance test 140 is passed, the top-down weights ($T_{ji}$) and bottom-up weights ($B_{ij}$) between the $F_1$ layer 230 and the $F_2$ layer 240 are adapted according to Equations (35) and (36), and the weights between the $F_2$ layer 240 and the Map Field 130 are updated by the following equation:

$$\omega_{j*k} = Y_k \tag{39}$$

The step of updating the top-down weights ($T_{ji}$) and the bottom-up weights ($B_{ij}$) is shown in block 580.

For the bottom-up and top-down weights, the weight adaption process is done iteratively for each training pattern. This is because the normalized input vector 210, represented by p, is also updated after each update iteration is made. Then, the new vector p in the $F_1$ layer 230 is used for the next weight update iteration (see Equations (35) and (36)).

During the training phase, both input vector 210 (i.e., AR parameters) and target output vector 220 (i.e., fault class) are presented to the network. Then the network starts to learn the association between the input vector 210 and the target output vector 220 according to the procedure described above. During the diagnosis phase, only an input vector 210 is provided to the network. The node in the $F_2$ layer 240 which passes the $F_1$ vigilance test 250 represents the network's output (i.e., predicted fault class).

Another unique function of the modified ARTMAP network 200 is its "unlearn" capability. In contrast to the network learning capability, the "unlearn" procedure removes "undesired" knowledge that has previously been learned by the network. This is very useful when a previously learned pattern is found to be a wrong pattern. In such a situation, one way to correct this mistake is to retrain all the patterns except the undesired one, which is not very feasible. A more efficient way to unlearn a pattern is to reset the network weights disregarding the incorrect pattern.

Generally, the "unlearn" procedure is the same as the training procedure describe above. Once an $F_2$ node passes both vigilance tests 240, 140, the network weights are adapted according to the following equations:

$$B_{ij^*} = \frac{1}{(1-d)\sqrt{N}} \quad (40)$$

$$T_{j^*k} = 0 \quad (41)$$

where N is the number of nodes in the $F_1$ layer 230 and d is a constant between 0 and 1.

The map field 230 weights are updated from the following equation:

$$w_{j^*k} = 0 \quad (42)$$

4.2.2. Diagnosis by the Modified ARTMAP Network

Figure 6:
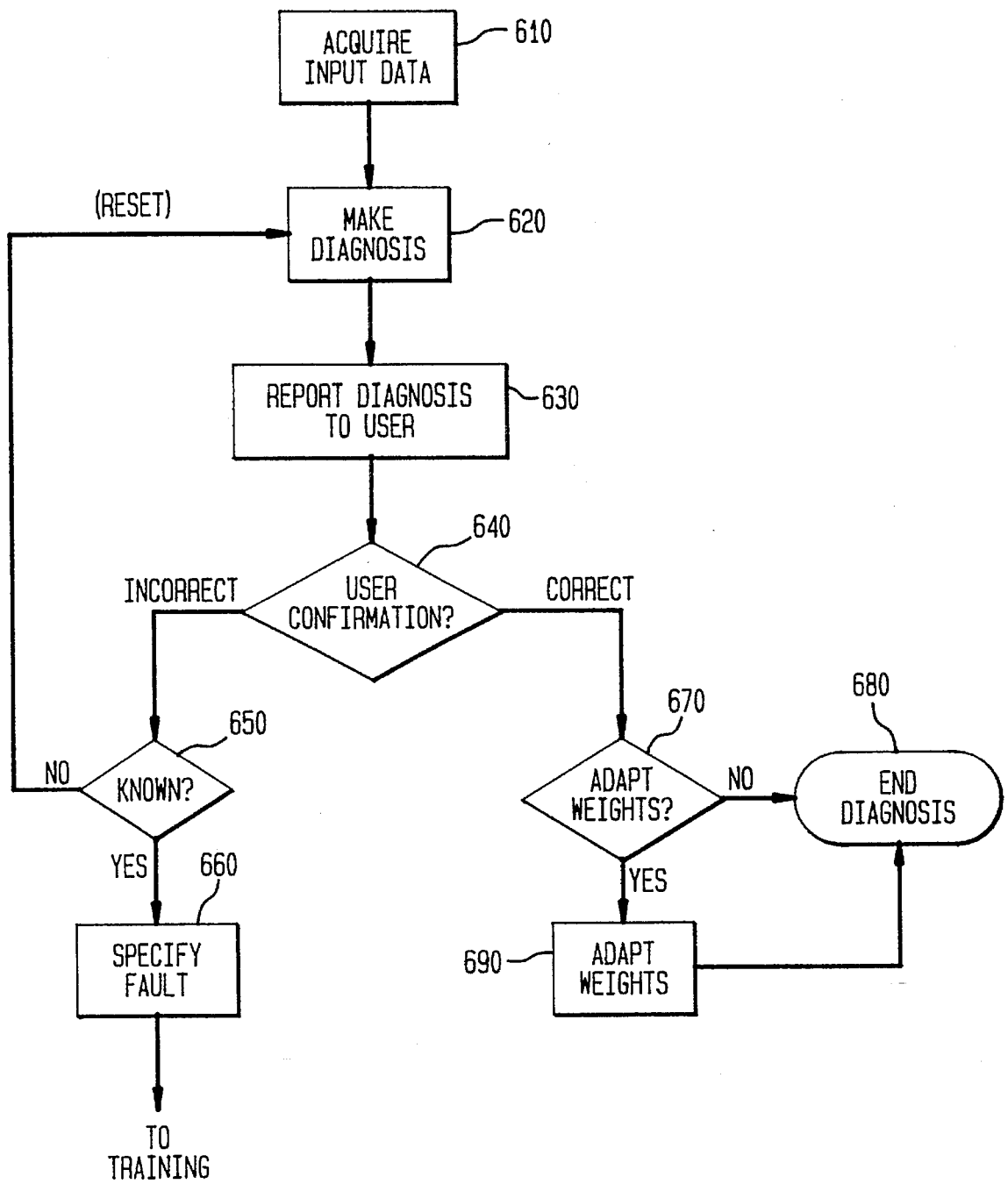
FIG. 6 illustrates a network diagnosis procedure.
Figure 8:
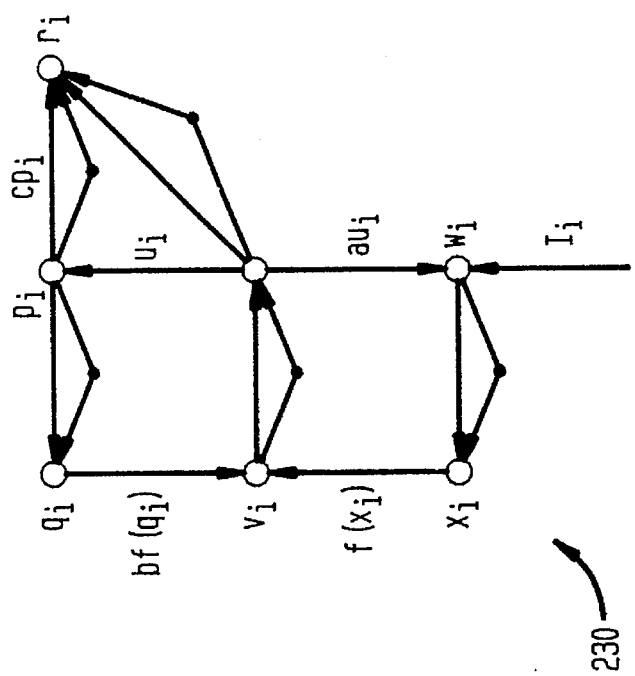
FIG. 8 is a more detailed illustration of the $F_1$ layer of the modified. ARTMAP network.

The network diagnosis procedure is illustrated in FIG. 6. Diagnosis takes place after the modified ARTMAP network 200 has been trained using the procedure described above. As shown in block 610, the modified ARTMAP network 200 initially acquires input data from a user or directly from a physical machine or process. After receiving an input, the ART 2 network 225 hypothesizes a diagnosis, as shown in block 620. If the hypothetical diagnosis passes the first vigilance test 250, the diagnosis result is reported to the user, as shown in block 630. In block 640, the user is asked to confirm the network diagnosis. If the diagnosis is correct, the user can either select to train the network with the present input pattern, i.e., ask the network to adapt its weights, or quit the diagnosis process, as shown in blocks and 680 respectively. If the diagnosis is found incorrect, two options are available. The user may specify, as shown in block 660, the correct fault classification and train the network if he/she knows the correct fault classification, or the user may request the network to make another diagnosis (i.e., return to block 620).

In order to test the system, a total of 48 data sets and three different machine conditions (i.e., normal, bearing failure, and misalignment) were used and divided into two parts: 15 data sets for training and the rest of the data sets for testing. The effects of the vigilance value and the training set size were also investigated. The performance of the network remained the same when the vigilance was set to 0.3, 0.5, 0.7, 0.8, or 0.9. However, when the training set size was set to 3 (one for each category), the network achieved about 97% accuracy. Once the training set size was increased to 6 (two for each category), the network was able to correctly identify all the test data.

4.3. Hypothesis and Test for Unknown Patterns

As discussed above, the primary technique used for machine fault diagnostics is the modified ARTMAP network 200 (or FDN). As mentioned previously, a network is first trained with examples so that the network is able to recognize a pattern when it has characteristics similar to one of the examples. However, there are times when a totally new pattern develops and the modified ARTMAP network 200 has not "experienced" such a pattern previously. Under such circumstances, the modified ARTMAP network 200 will be forced to diagnose an "unknown pattern." In order to overcome this problem, physical bearing models and fuzzy logic are melded in a preferred embodiment to perform a hypothesis and test procedure for analyzing and pinpointing the unknown fault situations.

Physical bearing models can be used as a means to provide preliminary training data of common bearing defects for the fault diagnostic network when the machine is brand-new or no historical sensory data is available. The theoretical equations for calculating bearing defect vibration signal frequencies are listed in Appendix A. It should be noted that physical bearing models are used as an illustration only. Other physical models may be used in accordance with the teachings of the present invention as would be apparent to a person skilled in the relevant art.

Physical bearing models can also be used as a hypothesis and test mechanism for complex or multiple faults conditions. Normally, the fault reasoning process in a complex problem involves uncertainties and ambiguities. One of most effective tools for taking fuzziness into consideration is the fuzzy logic methodology (Li, J. et al., "Fuzzy Cluster Analysis and Fuzzy Pattern Recognition Methods for Formation of Part Families (NAMRC)," *Society of Manufacturing Engineers*, 1988, pp. 558–300). As a consequence, the hypothesis and test mechanism of the present invention is implemented based on the fuzzy logic methodology.

FIG. 9 illustrates the fuzzy logic-based hypothesis and test procedure implemented according to the preferred embodiment of the present invention. This procedure is invoked when the modified ARTMAP network 200 encounters an unknown signal. It starts with retrieving bearing geometry parameters, as well as the shaft speed, for calculating the corresponding bearing defect frequencies using the equations in Appendix A, as shown in block 910. Each defect signal is combined with normal vibration signals to generate a set of fault signatures, as shown in block 920. These signatures are then fitted by an AR model to create a set of AR parameters, as shown in block 930. A reference (virtual) pattern for each bearing defect is generated by averaging a set of AR parameters for that defect, as shown in block 940.

Hypothesis and test is then carried out, as shown in block 950, with the following fuzzy logic methodology. It first assigns a fuzzy membership function to the parameters for each reference pattern. A linear membership function, as shown below, is used, where a and b are appropriate ranges of the parameter value.

$$\mu(x) = \begin{cases} 1.0 & b < x \\ \frac{(x-a)}{(b-a)} & a < x \leq b \\ 0.0 & x \leq a \end{cases} \quad (43)$$

Then, the fuzzy logic unit 950 hypothesizes possible defects and tests the hypotheses by comparing the similarity between the reference patterns and the unknown vibration signal. The similarity between pattern $X_i$ and $X_j$ is defined as follows:

$$(X_i,X_j) = 1 - \frac{\sum_{k=1}^{p} m|\mu_k(X_{ik}) - \mu_k(X_{jk})|}{\sum_{k=1}^{p} (\mu_k(X_{ik}) + \mu_k(X_{jk}))} \quad (44)$$

where p is the number of AR parameters in the pattern and m is a weighting factor for increasing the distance between sample reference patterns. A similarity score close to 1 means that the two patterns are very similar, and vice versa. The hypothesis and test procedure described above is programmed to list all identifiable possible faults and their similarity are presented to the user for further confirmation, as shown in block 960.

4.4. Fault Reasoning Expert System

In a preferred embodiment, the diagnostics system 400 is implemented with a Fault Reasoning Expert System (FRES). Any data sample with a suspected abnormal condition not detected with full confidence by the modified ARTMAP network 200 is sent to the FRES for analysis. Similarly, if the modified ARTMAP 200 suspects more than one type of fault (e.g., out of alignment and contamination) then the data sample is sent to the FRES.

The FRES checks the identifiable possible faults against it rules in its knowledge base, the damage or repair history, and machine usage information to determine likely faults. The result of this check is displayed via the user interface 450 along with recommendations.

Given below is a list of expert rules for general machine failures used by the FRES.

IF a series of frequencies are generated AND integer fraction subharmonies of running speed exist (½, ⅓, ¼, ..., ⅟ₙ) AND high frequencies are excited AND the waveform is truncated and flattened THEN the machine condition is ROTOR RUB.

IF vibration frequencies are significant at 0.42–0.48× RPM AND the vibration exists in the RADIAL direction THEN the machine condition is OIL WHIRL INSTABILITY.

IF 1×RPM in the RADIAL direction dominates the vibration spectrum AND the signal is in-phase and steady AND the amplitude due to unbalance increases by the SQUARE OF SPEED (3×speed increase=9×higher vibration) THEN the machine condition is FORCE UNBALANCE.

IF 1×RPM is dominant AND amplitude increases with the SQUARE OF SPEED AND the signal tends toward 180° out-of-phase AND high AXIAL and RADIAL vibrations occur THEN the machine condition is COUPLE UNBALANCE.

IF high 1×RPM occurs in both AXIAL and RADIAL directions AND AXIAL readings are in phase AND RADIAL readings are unsteady AND RADIAL readings are lower than AXIAL readings THEN the machine condition is OVERHUNG ROTOR BALANCE.

IF high AXIAL vibration with AXIAL phase differences near 180° AND the dominant vibration is 1×RPM or 2×RPM THEN the machine condition is BENT SHAFT*.

IF the largest vibration occurs at 1×RPM AND comparative horizontal and vertical PHASE readings differ by 0° or 180°. AND balancing attempt results in reducing VIBRATION in one direction, but increasing it in the other RADIAL direction THEN the machine condition is ECCENTRIC ROTOR.

IF high AXIAL vibration exists AND the vibration is 180° out-of-phase across the coupling AND the AXIAL vibration is high at both 1×RPM and 2×RPM but neither 1×, 2×, or 3×dominates the others THEN the machine condition is ANGULAR MISALIGNMENT.

IF dominate vibration is at 2×RPM AND subharmonic multiples of exactly ½ or ⅓×RPM (0.5×, 1.5×, 2.% ×, etc.) occur AND if the vibration occurs in the RADIAL direction THEN the machine condition is LOOSENESS.

IF the vibration spectrum is a SINGLE FREQUENCY (indicating sinusoidal motion) AND the AMPLITUDE of the vibration varies PROPORTIONALLY to the SQUARE of the speed THEN the machine condition is IMBALANCE**.

IF the vibration signatures in the RADIAL direction are GREATER THAN OR EQUAL to 1⅓ times the vibration signatures in the AXIAL direction THEN the machine condition is MISALIGNMENT.

* Bent shaft is only recognizable by studying phase

** Imbalance is only recognizable in the radial direction.

The expert rules for bearing failures are given below.

IF a series of running speed harmonies (up to 10 or 20) occur in the RADIAL direction AND vertical amplitudes are high relative to horizontal amplitudes AND the amplitude tends to decrease at high harmonies THEN the bearing condition is SLEEVE BEARING WEAR.

IF the amplitude at 2×RPM is GREATER THAN OR EQUAL TO ⅓ the amplitude at 1×RPM THEN the bearing condition is LOOSENESS.

IF considerable axial vibration exists AND twisting motion results with approximately 180° phase shift to bottom and/or side to side measured in the AXIAL direction AND vibration occurs at 1×RPM and 2×RPM AND 2×RPM dominates 1×RPM THEN the bearing condition is MISALIGNED BEARING.

IF a sharp pulse occurs at the BALL PASS FREQUENCY, obvious in the time series signal AND the frequency spectrum displays extremely low amplitudes THEN the machine condition is SINGLE SPALL on bearing race.

IF there is NO change in the VIBRATION FREQUENCIES with a change in SHAFT SPEED THEN the machine condition is RUB or RESONANCE.

IF the FFT transforms the vibration signal into a SQUARE WAVE THEN the bearing condition is SEVERE LOOSENESS.

The expert rules for gear failures are given below.

IF the pattern of gear mesh is a SINE wave or MODIFIED SINE wave at the GEAR MESH FREQUENCY AND the vibration frequency occurs at 1×and 2×RPM AND the gear mesh frequency exists with SIDEBANDS AND all peaks are of low amplitudes THEN the gear condition is NORMAL.

IF a high amplitude exists at 1×RPM AND gear natural frequency is sidebanded at running speed AND the time waveform shows a pronounced spike when the tooth meshes with the teeth on the mating gear THEN the gear condition is a BROKEN TOOTH.

IF a vibration frequency exists at 1×RPM AND vibration sum and difference frequencies exist at ±1×RPM THEN the gear condition is GEAR RUNOUT.

IF sidebands are at the same AMPLITUDE as the FUNDAMENTAL FREQUENCY THEN the GEAR needs REPLACING.

IF the GEAR NATURAL FREQUENCY is excited along with sidebands spaced at the running speed of the bad gear AND high amplitude sidebands surrounding the GEAR MESH FREQUENCY occur THEN the gear condition is TOOTH WEAR.

IF high amplitude sidebands occur around the GEAR MESH FREQUENCY AND the GEAR MESH FREQUENCY is excited AND the GEAR NATURAL FREQUENCY is excited AND the GMF and GNF are sidebanded at 1×RPM THEN the gear condition is GEAR ECCENTRICITY AND BACKLASH.

IF SECOND or HIGHER harmonies of the GEAR MESH FREQUENCY are excited AND the harmonies are sidebanded at RUNNING SPEED AND a small amplitude exist at 1×GMF AND higher amplitudes exist at 2×or 3×GMF THEN the gear condition is GEAR MISALIGNMENT.

IF a spike is displayed at 1×RPM THEN the gear condition is GEAR OUT OF BALANCE or MISSING TOOTH.

* gear mesh frequency=number of teeth×gear speed

Of course, as should be apparent to one skilled in the relevant art, other expert rules can be implemented. That is, the expert rules given above should not be considered an exhaustive list, but rather illustrative of the expert rules used in a preferred embodiment of the present invention.

4.5. Fault Diagnostics

Referring to FIG. 15a, a physical machine or process is operated and the diagnostic procedure can begin. Initially, data (e.g., vibration, temperature, pressure) is acquired from the physical machine or process, as shown in block 1505. This data is preprocessed using an AR model, as shown in block 1510.

Next, the parameter produced by the AR model is used to detect abnormal conditions in the physical machine or process. This detection is done on-line using indices based on a RMS measurement and a covariance statistic of EWMA method, as shown in block 1515. This step can be considered a filter for the fault diagnostic network 200. If block 15 15 does not detect a fault, fault diagnostics does not begin. This feature of the present invention is shown in block 1520. Block 1520 monitors the output of block 1515 and determines from this output whether the machine or process is operating in a normal manner (green condition), a potentially problematic manner (yellow condition), or a dangerous manner (red condition). Each of these conditions are implementation specific, and can be adjusted as required by the particular system or process being operated as should be apparent to a person skilled in the relevant art.

If the machine or process is operating in a green condition, the user interface 450 connected to the diagnostic system 400 displays an indication that the machine or process is operating normally, as shown in block 1525. The machine or process is stopped if it is operating in a red manner, as shown in block 1530. After stopping the machine or process, diagnostics are performed. Similarly, if the RMS and EWMA indicate that a yellow condition exists then diagnostics are performed.

Referring to FIG. 15b, if a yellow or red condition exists diagnostics are performed, as shown in block 1535. In a preferred embodiment, additional sensory data is acquired from the machine or process under review, as shown in block 1540. Note that this is an additional step that is not required. The data originally used by block 1515 to detect a fault can be used for diagnostics.

Next, the data is presented to the FDN 200 (modified ARTMAP network 200), as shown in block 1545. Of course, the FDN 200 has previously been trained using the procedure outlined above. Decisional block 1550 determines whether the FDN 200 has provided a diagnosis (i.e., identified a fault with the machine or process). If the FDN 200 is not able to provide a diagnosis, physical machine (or process) models are applied, as shown in block 1555. As discussed above, the physical models are generated from defect frequencies generated from known theoretical equations that are combined with normal signals taken from the machine or process under normal operating conditions. This combination results in a set of fault signatures.

Next, the fuzzy logic methodology is applied to the fault signatures, as shown in block 1560. Note that even if the FDN 200 provides a diagnosis fuzzy logic is still applied to the diagnosis as a secondary check. The fuzzy logic first hypothesizes possible faults and tests the hypotheses by comparing the similarity between the fault signatures and the unknown signals from the machine and process. Subsequently, the diagnostic system 400 displays all identifiable possible faults, as shown in block 1565.

These identifiable possible faults are provided to a FRES, as shown in block 1570. As described above, the FRES checks the identifiable possible faults against the rules in its knowledge base, the damage or repair history, and machine usage information to determine likely faults. The result of this check is displayed via the user interface 450 along with recommendations, as shown in block 1575.

At this time, an operator can intervene, as shown in block 1585. Finally, the database 440 is updated with the final results from the diagnostic procedure outlined above.

5. Transputer Network

In a preferred embodiment, the present invention implements the modified ARTMAP network 200 (or FDN) diagnosis and training, as well as the fuzzy logic-based hypothesis and test procedures, on a transputer network. The demand for higher performance computers has increased significantly because of the advances in technology which enable sensors to produce more data and make systems more sophisticated. Almost all the computers that are on the market today are so-called sequential or von Neumann computers where each instruction is individually interpreted and executed before the next one may begin. Therefore, the speed of this class of computer system is ultimately determined by the CPU power of the system.

Recent studies have shown that parallel computing based on PC-class microprocessors outperforms vector machines in performance and cost. Parallel computing utilizes a number of CPUs to perform multiple tasks simultaneously. These CPUs can be linked together in many ways allowing a wide variety of parallel processing architectures.

A Multiple Instruction-stream Multiple Data-stream (MIMD) (i.e., several CPUs simultaneously execute different instructions on different data) machine known as a transputer cluster has been specifically developed for parallel processing over the years. A transputer is a 32-bit computer chip that is a complete computer with its own CPU and local memory. Each transputer has four serial links for interprocessor communications. Through the links, a transputer can be connected with other transputer units to form a high performance concurrent system. In addition, networks of transputers can have any desired topology, such as pipeline, tree, and array structure, which means that they have the flexibility to suit a wide range of applications.

In a preferred embodiment, The FDN was implemented on a 486 personal computer and a network of four transputers. Time-consuming computational tasks are designed to perform on the transputer network, such as neural network training and diagnosis, and fuzzy logic-based hypothesis and test procedures. The 486-PC works as a host computer for job assignment, activity coordination, user interface, and data acquisition. A number of machines or components can be monitored using this system.

Described below is the hardware and software configurations of the transputer network utilized by the preferred embodiment and the implementations of the FDN diagnosis and training procedures, as well as fuzzy logic-based hypothesis and test procedure, on the transputer network. This performance of these procedures on the transputers is evaluated and compared with the performance on a 486 PC.

The parallel processing hardware used in a preferred embodiment is MicroWay's Quadputer board. The Quadputer is a single slot, AT form factor board that includes the control logic for four T800-25 transputers, each with four megabytes of external memory for a total of sixteen megabytes on a board. The speed of each transputer is 25 MHz.

Figure 10:
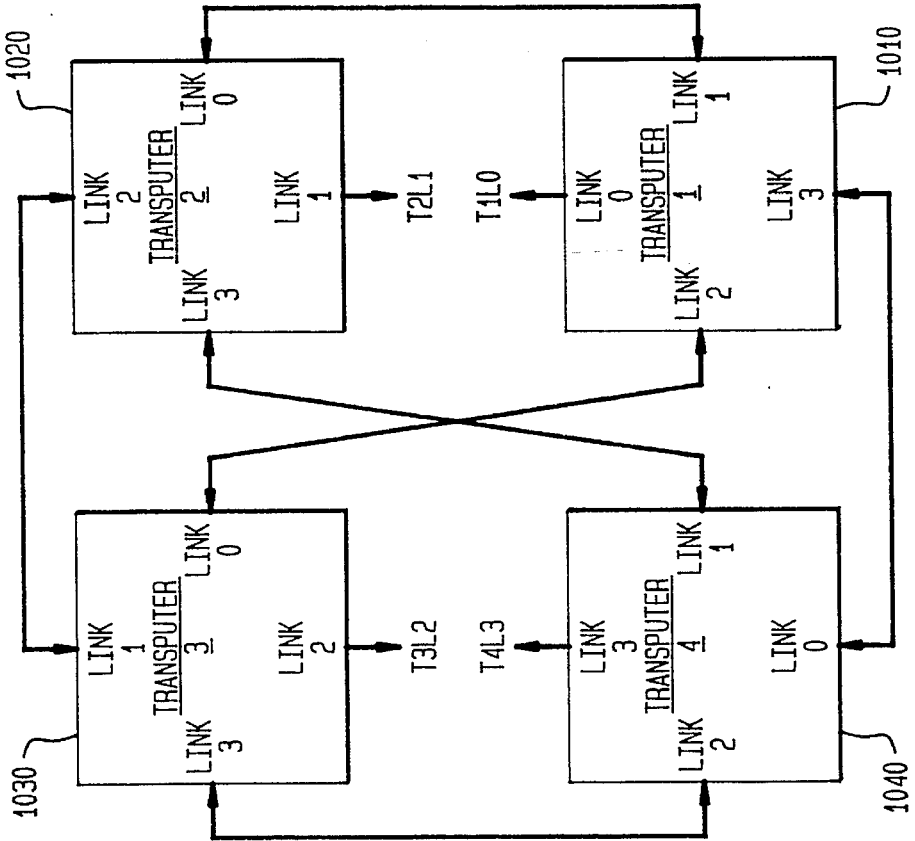
FIG. 10 illustrates the physical connections of four transputers on a Quadputer board.

Because each transputer node on the board has its own local memory which cannot be accessed directly by other transputers, it is necessary to communicate directly by actively sending and receiving information across the connections between transputers. FIG. 10 illustrates the physical connections of the four transputers 1010–1040 on the Quadputer board.

This network of transputers 1010–1014 can be configured into different configurations, such as pipeline and tree, because each transputer has a connection with the other three transputers. For example, in the tree configuration, Transputer 1 1010, sometimes being referred to as "root" transputer, is connected to Transputer 2 1020, Transputer 3 1030, and Transputer 4 1040 via Links 1, 2, and 3, respectively.

It can also be seen from FIG. 10 that there are four uncommitted links, T1L0, T2L1, T3L2, and T4L3. These links can be used to connect with other transputer boards or to produce multiple connections between two transputers on the same board except for T1L0 which is dedicated to connection with the host computer (not shown). Therefore, the role of the root transputer 1010 is very important since it has to interface with the host computer to perform data I/O functions. In other words, all the information in the other transputers has to transfer to the root transputer 1010 first in order to be displayed on the host computer. In a preferred embodiment, a 486 PC running at 33 MHz is used as the host computer. Of course, other computers can be used as will become apparent to those skilled in the art.

Figure 13:
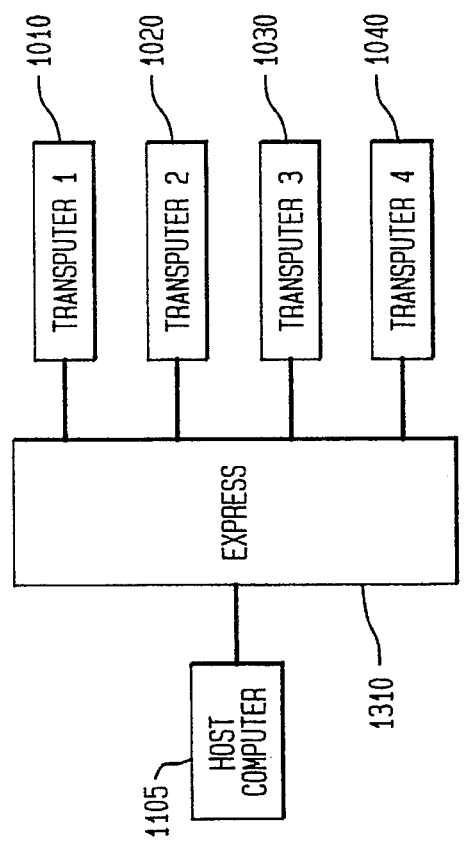
FIG. 13 shows the architectural diagram of the transputer based approach that includes the software package Express.

Because every information transfer has to go through the root transputer 1010, the complexity of communications in the network is increased. Hence, a programmer has to be fully aware of the derailed communications in the network, such as which node is connected to which via which link, while implementing a parallel program on the network. In order to resolve this problem, a communication package called Express 1310 is used by the present invention, as shown in FIG. 13. Express 1310 is available from ParaSoft Sells Corp., 27415 Trabuco Circle, Mission Viejo, Calif., 92692, (714) 380-9739. With this package, any transputer is able to send/receive messages directly to/from each other as well as the host computer 1050, regardless of the specific hardware or configuration involved. FIG. 13 shows the hardware structure with Express 1310 through which the host PC 1105 and all the transputer nodes are connected to one another.

There are two programming models provided by Express 1310, one is the Cubix model and the other is the "Host-Node" model. The Cubix model is conceptually the simplest. In this model, the parallel program including data and file I/O, graphics, user interface, etc. has to be loaded and executed on the transputer nodes. The advantage of this approach is that the program is easy to debug, expand, and maintain. The disadvantage of this approach is that it may require more memory than is available on the transputer nodes.

The "Host-Node" model entails writing a program to run on the host computer which coordinates and controls the activities on the transputer nodes. In this model, all the I/O has to be handled by the host program and then sent in messages to the transputer nodes. The advantage of this approach is that the I/O speed is faster; in addition, it is able to provide a more complex graphical user interface. These two properties are crucial for application purposes. Moreover, it may be wasteful to port the developed graphical user interface and data acquisition codes to the transputer environment under the Cubix model when it may run intact on the host computer. Therefore, the "Host-Node" model is used as the programming model in a preferred embodiment.

In a preferred embodiment, the programming language used for the host PC 1105 is Turbo C++, and the parallel programs for the transputer nodes are written and complied using Logical Systems C.

Figure 14A:
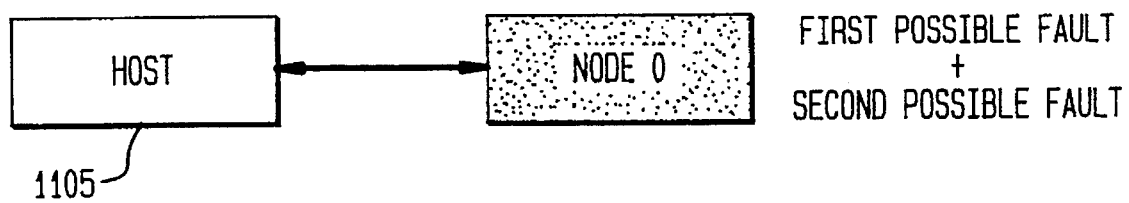
FIG. 14 shows a transputer implementation of a fault diagnostics procedure.
Figure 14B:
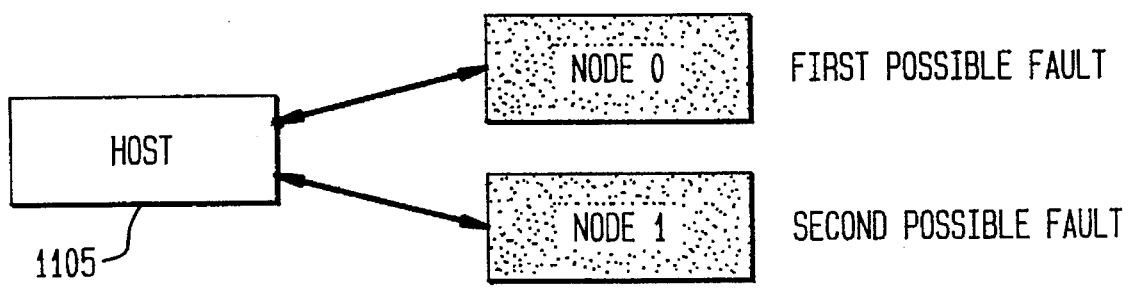

As described above, the diagnosis procedure of the modified ARTMAP network 200 is designed to find the two most likely faults for each pattern which is presented to the network 200. Searching for these two possible faults is done sequentially on the 486 PC which means that modified ARTMAP network 200 finds the first node in the $F_2$ layer which passes the vigilance test 250 as the first possible fault, then finds the next one as the second possible fault. In a preferred embodiment, this procedure is implemented on transputers. FIG. 14 shows a transputer implementation of the FDN diagnosis procedure.

It has been shown that a single T800-25 transputer is much slower than a 486 PC. This is not only because the CPU speed of the T800-25 transputer is slower than the 486 PC, but also because there is a communication overhead involved in the transputer implementation. However, the parallel processing advantage of transputers becomes significant when comparing the efficiency of using one transputer to that of using two transputers. The efficiency of diagnosis increases about 42% (from 0.19 second to 0.11 second). Besides, the performance of using two transputers in diagnosing five patterns is the same as that of a 486 PC.

Furthermore, the deviation of diagnosis times is larger for transputers. Transputers tend to take more time at the first attempt. This is because all the network information has to be transferred the first time while only the input vector has to be transferred thereafter.

The most time-consuming task in the modified ARTMAP network 200 training procedure (Shown in FIG. 5) is the adaptation of bottom-up weights ($B_{ij}$) and top-down weights ($T_{ji}$). This is because the weights adaption is performed iteratively for each training pattern. As described below, the procedure of the FDN weight adaption is implemented on a transputer network.

Figure 11A:
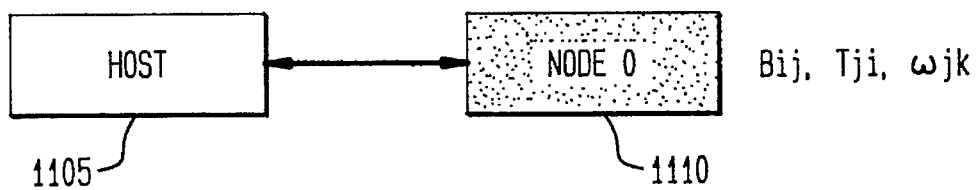
FIG. 11 illustrates a transputer implementation of the fault diagnostic network training procedure.
Figure 11B:
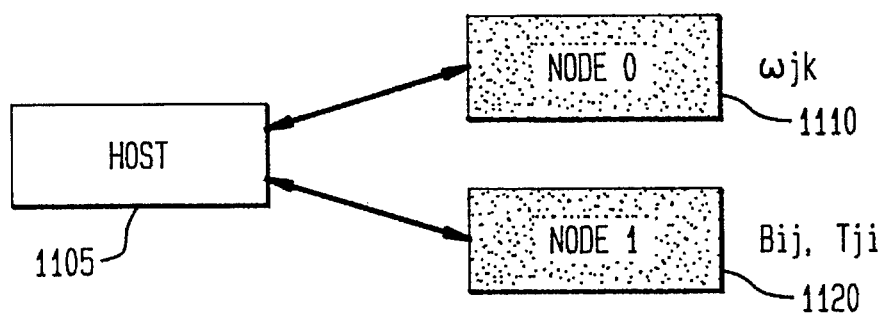
Figure 11C:
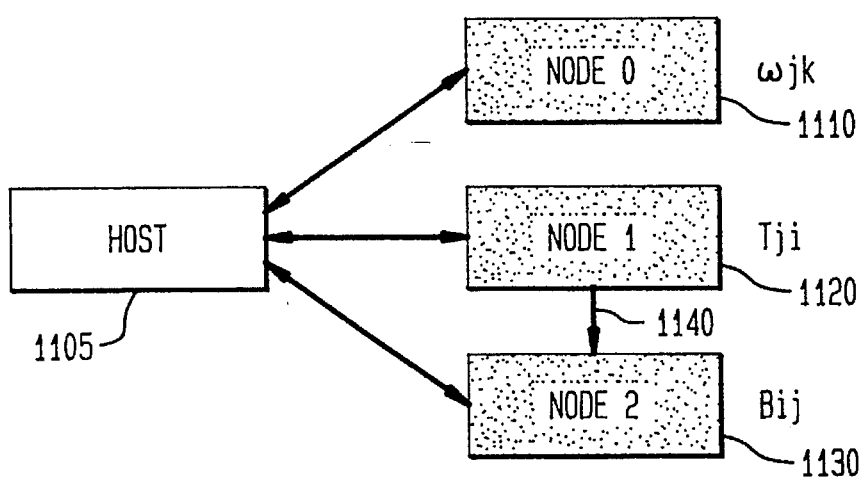

Transputer implementation of the modified ARTMAP network 200 training procedure is illustrated in FIG. 11. Different ways of implementation were considered; the uses of one, two, and three transputers to search for a node in the $F_2$ layer which passes both vigilance tests 240 and 250 and performs the weight adaption procedure. In the first case, all the weight adaptions are performed sequentially on one transputer 1110. In the second case, the update of weights between the $F_2$ layer 240 and the Map Field 130 is carried out on a first transputer 1110 while bottom-up and top-down weights adaption are done on a second transputer 1120. Then, bottom-up and top-down weights are further separated to work on two transputers 1120, 1130 in the last case. As mentioned above, the normalized input vector p in the $F_1$ layer 230 is updated every time each weight update iteration is made. Hence, in the second transputer 1120, calculations of vector p is performed after the top-down weights are updated. Then, the new updated vector p is sent to the third transputer 1130 to be used for bottom-up weight adaption (see Equation (35)). Therefore, there is a single direction communication link 1140 from transputer 1120 to transputer 1130.

The programming logic for this procedure on transputers is the same as the diagnosis. The only difference is that both target output vector 220 and the weights between the F2 layer 240 and the Map Field 130 have to be sent to the transputers.

It has been shown that a 486 PC is much faster than the other three transputer implementation configurations. In addition, the improvement of training performance from the use of one transputer to two transputers is not significant (about 5%). The worst training performance happens when three transputers are used. It is almost three times slower than the 486 PC. The reason for this low training speed is that there is a large communication overhead involved between nodes 1 and 2.

As for the deviation in training time, the 486 PC has a larger deviation. This is because the number of network resets tends to be higher for later training patterns, which means more training time is needed. However, the deviation for the transputer is not as large as the 486 PC since there is a communication overhead involved in training. Therefore, later tests took longer.

An alternative embodiment uses multiple processors by having both host PC and transputers work in parallel. When the host PC finishes file and data I/O for the first training pattern, it continues to receive the information for the next training pattern from the user, while transputers receive the data from the host PC and start the training process. The total I/O and training time reduction from this approach after five tests is about 12.6% (from 45.02 second to 39.35 second).

Described below is a transputer implementation of the fuzzy logic-based hypothesis and test procedure. As described above, the use of this procedure is to perform deep fault reasoning for the patterns that the fault diagnostic network is not able to recognize. The fuzzy logic-based hypothesis and test procedure first generates, for example, six reference patterns based on the given bearing parameters, machine running condition, and baseline vibration signature, then compares those generated patterns with the given unknown vibration signature to determine the similarity among them.

Figure 12A:
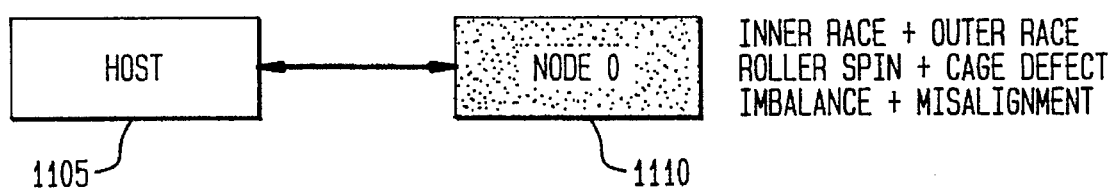
FIG. 12 illustrates a transputer implementation of the hypothesis and test procedure using one transputer and three transputers.
Figure 12B:
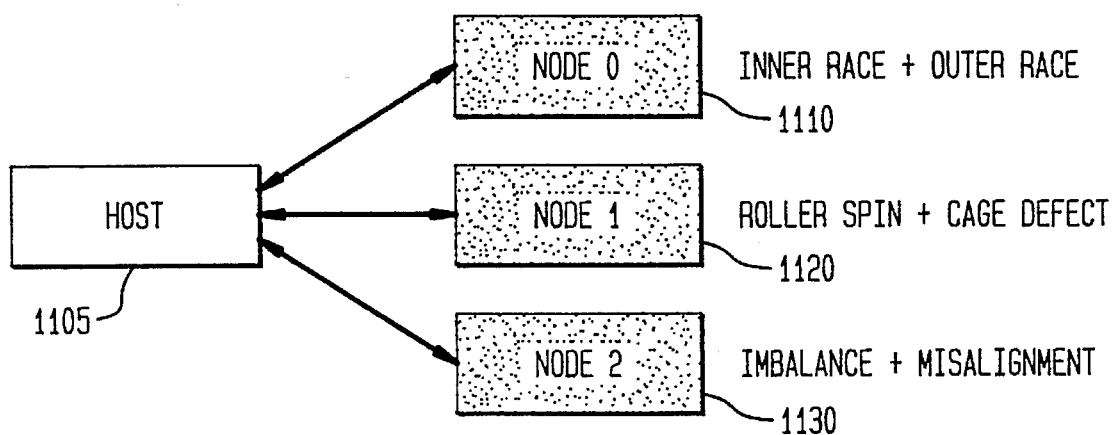

FIG. 12 shows transputer implementations of the hypothesis and test procedure using one transputer and three transputers. For the case of using one transputer, the generation and comparison of all six bearing defects are done sequentially on a single transputer 1110. For the case of using three transputers 1110–1130, all the transputers work in parallel with each one of them assigned to work on two defect patterns. The host transputer 1105 is responsible for I/O and the user interface, as well as sending bearing parameters, machine running condition, etc., to the transputer nodes and receiving the outputs (i.e., similarity) from all three transputers 1110–1130.

It has been shown that the 486 PC is faster than a single transputer. However, when the task is divided into three pieces performed by three transputers, the average time reduction is about 37% (from 0.60 second to 0.38 second). The performance of the hypothesis and test procedure can be greatly improved if more defects are included in the model and, at the same time, more transputers are used to implement the procedure.

6. Conclusion

More and more manufacturing companies are adopting predictive maintenance in their maintenance programs today. The fault diagnostic system presented herein provides an effective predictive maintenance program. With the capability of performing robust and on-line fault diagnostics, the system is able to reduce machine downtime and costs dramatically.

While the invention has been particularly shown and described with reference to preferred embodiments thereof, it will be understood by those skilled in the art that various changes in form and details may be made therein without departing from the spirit and scope of the invention.

Appendix A

Physical Beating Models

The following is a list of theoretical equations for calculating bearing defect vibration signal frequencies [See Braun, S., Mechanical Signature Analysis: Theory and Applications, Academic Press, London, 1986; Sandy, J., "Monitoring and Diagnostics for Rolling Element Bearings," Sound and Vibration, June 1988, pp. 16–20]:

$$f_{ir} = \frac{N}{120} (n) \left( 1 + \frac{d}{D} \cos \alpha \right) \quad (A.1)$$

$$f_{or} = \frac{N}{120} (n) \left( 1 - \frac{d}{D} \cos \alpha \right) \quad (A.2)$$

$$f_c = \frac{N}{120} (n) \left( 1 - \frac{d}{D} \cos \alpha \right) \quad (A.3)$$

$$f_{rs} = \frac{N}{120} \left( \frac{D}{d} \right) \left[ 1 - \left( \frac{d}{D} \cos \alpha \right)^2 \right] \quad (A.4)$$

$$f_m = \frac{N}{60} (n) \pm 2 \left( \frac{N}{60} \right) \quad (A.5)$$

$$f_{im} = \frac{N}{60} \quad (A.6)$$

where

N=shaft speed (CPM)

n=number of rotating elements d=rolling element diameter

D=bearing pitch diameter (to roller center)

α=contact angle $f_{ir}$=inner race defect $f_{or}$=outer race defect $f_c$=cage defect $f_{rs}$=roller spin $f_m$=misalignment $f_{im}$=shaft imbalance

What is claimed is:

1. A fault diagnostic system, comprising:

(a) a data acquisition module that collects sensory signals;

(b) a diagnostic module, connected to said data acquisition module, that performs on-line fault detection for a physical machine or process, fault diagnostics, and provides recommendations in regard to said on-line fault detection and said fault diagnostics; and (c) a machine model module, connected to said diagnostic module, that provides a physical model for identifying fault conditions that cannot be diagnosed by said diagnostic module.

2. The fault diagnostic system of claim 1, wherein said data acquisition module includes a plurality of sensors each capable of real-time data acquisition.

3. The fault diagnostic system of claim 1, wherein said diagnostic module includes a parametric modeling module, a modified ARTMAP neural network, a fuzzy logic module, and an expert system.

4. The fault diagnostic system of claim 3, wherein said machine model module includes physical models for bearing and gears, and provides data for preliminary training of said modified ARTMAP neural network.

5. The fault diagnostics system of claim 1, wherein said data acquisition module includes means for preprocessing said sensory signals using an autoregressive model.

6. The fault diagnostic system of claim 1, wherein said diagnostic module comprises detection means for performing fault detection that includes detecting abnormal conditions in said physical machine or process by using an overall root mean square (RMS) measurement and a covariance statistic of an exponentially weighted moving average method (EWMA), wherein a control limit is set for said RMS and said EWMA, and if said sensory conditions exceeds said control limit than an abnormal condition exists.

7. The fault diagnostic system of claim 1, wherein said diagnostic module comprises identification means for performing fault identification based on a model-based reasoning approach that includes fuzzy logic methodology.

8. The fault diagnostic system of claim 1, wherein said diagnostic module comprises an expert system that performs fault verification and that provides recommendations about detected faults to a user.

9. The fault diagnostic system of claim 1, wherein said diagnostic module and said machine model module are implemented on a transputer network.

10. The fault diagnostic system of claim 1, wherein said sensory signals include vibration signals, pressure signals, and/or temperature signals from said physical machine or process.

11. The fault diagnostic system of claim 1, wherein said diagnosis module comprises a fault diagnostic network, wherein said fault diagnostic network includes:
   (a) an ART module that accepts an input pattern, said ART module having a first layer and a second layer, and configured to perform a first vigilance test and generate a recognition category; and
   (b) a map field, connected to said ART module and to a target output pattern, that performs a mapping between said recognition category and said target output pattern, and triggers the performance of a second vigilance test;
   wherein said second vigilance test determines the closeness between said target output pattern and said recognition category.

12. The fault diagnostic system of claim 11, wherein said first layer comprises three levels that each include:
   means for performing integration of intrafield and interfield inputs to produce an integrated activation signal; and
   means for performing normalization of said integrated activation signal.

13. The fault diagnostic system of claim 11, wherein said ART module is an ART2 network that can accept binary or analog input patterns.

14. The fault diagnostic system of claim 11, wherein said target output pattern is a binary vector, wherein each node of said binary vector corresponds to a particular machine or process condition.

15. The fault diagnostic system of claim 11, further comprising parameter means for fitting a raw vibration signal collected from a machine under review to a predetermined parametric model, wherein said parameter means generates a parameter.

16. The fault diagnostic system of claim 15, further comprising a normalization module, connected to said parameter means, that removes meaningful negative values that said ART module is not able to recognize from said parameter.

17. The fault diagnostic system of claim 16, wherein said normalization module comprises:
   (1) means for dividing said parameter into a negative part and a positive part;
   (2) means for scaling said negative part and said positive part by dividing said parameter by a maximum parameter value.

18. The fault diagnostic system of claim 11, wherein each node of said second layer corresponds to a particular fault condition.

19. The fault diagnostic system of claim 1, wherein said machine model module further provides a deep fault reasoning mechanism to identify complex or multiple fault conditions.

20. A method for diagnosing a physical machine or process, the method comprising the steps of:
   (1) acquiring a first set of data from the physical machine or process;
   (2) preprocessing said first set of data using an autoregressive model, said preprocessing generating an autoregressive parameter; and
   (3) detecting abnormal conditions in said autoregressive parameter using an overall root means square (RMS) measurement and a covariance statistic of an exponentially weighted moving average (EWMA), wherein if an abnormal condition is detected then,
      (a) identifying whether said physical machine or process has a fault, including,
         (i) determining a hypothesis with the aid of a fault diagnostic network, and if said fault diagnostic network cannot generate a hypothesis, then
         (ii) determining a hypothesis with the aid of a model-based reasoning approach, wherein said model-based reasoning approach uses fuzzy logic; and
      (b) supplying said identifiable fault to a fault expert system having a knowledge base with a set of rules, wherein said fault reasoning expert system checks said identifiable fault against said set of rules.

21. The method of claim 20, wherein step (3) comprises the steps providing an indication to a user that said machine or process is operating in a normal manner, a potentially problematic manner, or a dangerous manner.

22. The method of claim 20, wherein said fault reasoning expert system also checks said identifiable fault against damage and repair history and machine usage information.

23. The method of claim 22, further comprising the step of displaying said identifiable fault along with recommendations via a user interface.

24. The method of claim 20, further comprising the steps of preprocessing said second set of acquired data using an autoregressive model, said preprocessing generating an autoregressive parameter, and normalizing said autoregressive parameter.

25. The method of claim 20, further comprising the step of acquiring a second set of data from said physical machine or process after said abnormal condition is detected.

* * * * *